US011505517B2

(12) United States Patent
Sedat et al.

(10) Patent No.: US 11,505,517 B2
(45) Date of Patent: Nov. 22, 2022

(54) METHOD FOR PURIFYING 1,1,1,2,3-PENTAFLUOROPROPANE AND USE THEREOF FOR OBTAINING HIGH-PURITY 2,3,3,3-TETRAFLUOROPROPENE

(71) Applicant: Arkema France, Colombes (FR)

(72) Inventors: Pierre-Marie Sedat, Pierre-Benite (FR); Collier Bertrand, Colombes (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 17/516,791

(22) Filed: Nov. 2, 2021

(65) Prior Publication Data

US 2022/0055973 A1 Feb. 24, 2022

Related U.S. Application Data

(62) Division of application No. 16/959,197, filed as application No. PCT/FR2019/050017 on Jan. 4, 2019, now Pat. No. 11,168,044.

(30) Foreign Application Priority Data

Jan. 8, 2018 (FR) ...................... 1850121

(51) Int. Cl.
  *C07C 21/18* (2006.01)
  *C07C 17/354* (2006.01)
  (Continued)

(52) U.S. Cl.
  CPC .............. *C07C 21/18* (2013.01); *C07C 17/25* (2013.01); *C07C 17/354* (2013.01); *C07C 17/383* (2013.01); *C07C 19/08* (2013.01)

(58) Field of Classification Search
  CPC ................ C09K 5/045; C09K 2205/22; C09K 2205/126; C07C 21/18
  See application file for complete search history.

(56) References Cited

U.S. PATENT DOCUMENTS 10,119,055 B2 * 11/2018 Boussand ............... C07C 21/18
2010/0029997 A1 2/2010 Wang et al.
(Continued)

FOREIGN PATENT DOCUMENTS

CN 103449963 A 12/2013
WO 03027051 A1 4/2003
(Continued)

OTHER PUBLICATIONS

ISA/EP; International Search Report and Written Opinion for International Patent Application No. PCT/FR2019/050017 dated Apr. 4, 2019, 11 pages.

*Primary Examiner* — Jafar F Parsa
(74) *Attorney, Agent, or Firm* — NK Patent Law

(57) ABSTRACT

The present invention relates to a process for purifying 1,1,1,2,3-pentafluoropropane, comprising the steps of: i) providing a composition A1 comprising 1,1,1,2,3-pentafluoropropane and 1,1,1,3-tetrafluoropropane; ii) purifying, preferably distilling, said composition A1 under conditions that are sufficient to form at least two streams including a first stream comprising 1,1,1,2,3-pentafluoropropane and a second stream comprising 1,1,1,3-tetrafluoropropane. The present invention also relates to a process for producing 2,3,3,3-tetrafluoropropene and a composition comprising 2,3,3,3-tetrafluoropropene.

5 Claims, 8 Drawing Sheets

(51) Int. Cl.
*C07C 19/08* (2006.01)
*C07C 17/25* (2006.01)
*C07C 17/383* (2006.01)

(56) References Cited

U.S. PATENT DOCUMENTS

2011/0021849 A1   1/2011   Avril et al.
2012/0065437 A1   3/2012   Merkel
2012/0083632 A1   4/2012   Guillet et al.
2017/0174591 A1*  6/2017   Wang .................... C07C 17/395

FOREIGN PATENT DOCUMENTS

WO   2008030439 A2   3/2008
WO   2010139873 A1   12/2010
WO   2011010025 A1   1/2011

* cited by examiner

US 11,505,517 B2

METHOD FOR PURIFYING 1,1,1,2,3-PENTAFLUOROPROPANE AND USE THEREOF FOR OBTAINING HIGH-PURITY 2,3,3,3-TETRAFLUOROPROPENE

CROSS-REFERENCE TO RELATED APPLICATIONS

This application is a Divisional application of U.S. application Ser. No. 16/959,197, filed on Jun. 30, 2020, which was a U.S. National Stage application of International Patent Application No. PCT/FR2019/050017, filed on Jan. 4, 2019, which claims the benefit of French Patent Application No. 1850121, filed on Jan. 8, 2018.

TECHNICAL FIELD OF THE INVENTION

The present invention relates to a process for purifying 1,1,1,2,3-pentafluoropropane. The present invention also relates to a process for producing 2,3,3,3-tetrafluoropropene from purified 1,1,1,2,3-pentafluoropropane. Finally, the present invention relates to the production of high-purity 2,3,3,3-tetrafluoropropene.

TECHNOLOGICAL BACKGROUND OF THE INVENTION

Hydrofluorocarbons (HFCs) and in particular hydrofluoroolefins, such as 2,3,3,3-tetrafluoro-1-propene (HFO 1234yf) are compounds known for their properties as refrigerants and heat-transfer fluids, extinguishers, propellants, foaming agents, swelling agents, dielectric gases, polymerization medium or monomer, support fluids, abrasive agents, drying agents and fluids for power production units. Unlike CFCs and HCFCs, which are potentially hazardous to the ozone layer, HFOs do not contain any chlorine and thus do not pose any problems for the ozone layer.

Several processes for manufacturing 1234yf are known.

WO 2011/010025 describes a process for preparing 2,3,3,3-tetrafluoro-1-propene, comprising the following steps: (i) gas-phase hydrogenation of hexafluoropropylene to 1,1,1,2,3,3-hexafluoropropane in the presence of a super-stoichiometric amount of hydrogen and of a catalyst in a reactor; (ii) dehydrofluorination of the 1,1,1,2,3,3-hexafluoropropane obtained in the preceding step to give 1,2,3,3,3-pentafluoro-1-propene in the presence of a dehydrofluorination catalyst or using a mixture of water and potassium hydroxide; (iii) gas-phase hydrogenation of the 1,2,3,3,3-pentafluoro-1-propene obtained in the preceding step to give 1,1,1,2,3-pentafluoropropane in the presence of a super-stoichiometric amount of hydrogen and of a catalyst in a reactor; (iv) purification of the 1,1,1,2,3-pentafluoropropane obtained in the preceding step; (v) dehydrofluorination of the purified 1,1,1,2,3-pentafluoropropane to give 2,3,3,3-tetrafluoro-1-propene in the presence of a dehydrofluorination catalyst or using a mixture of water and potassium hydroxide; (vi) purification of the 2,3,3,3-tetrafluoro-1-propene obtained in the preceding step.

WO 2010/139873 describes a dehydrofluorination process in the presence of a solid reagent comprising calcium hydroxide.

WO 2008/030439 describes a process for preparing hydrofluoroolefins from a fluoropropane compound in the presence of a basic solution, a solvent and a phase-transfer agent.

WO 03/027051 describes a process for preparing hydrofluoroolefins from a fluoropropane compound in the presence of an alkaline hydroxide and a phase-transfer agent.

CN103449963 describes a multi-step process for preparing 2,3,3,3-tetrafluoropropene notably comprising a dehydrofluorination step in the presence of an alkaline solution and an organic solvent. US 2010/0029997 describes a process for producing 2,3,3,3-tetrafluoropropene. This is obtained from 1,1,1,2,3-pentafluoropropane purified by photochlorination to remove certain impurities prior to performing the dehydrofluorination reaction.

There is a need for a process for preparing HFO-1234yf which makes it possible to limit the content of byproducts generated in the various steps of a process for manufacturing HFO-1234yf, notably impurities with a toxic potential: mention is made of 1,2,3,3,3-pentafluoropropene (1225ye), 1,2,2-trifluoroethane (143) and 3,3,3-trifluoropropene (1243zf). 1,2,3,3,3-Pentafluoropropene (1225ye) has a boiling point close to HFO-1234yf and is difficult to separate from HFO1234yf. 3,3,3-Trifluoropropene has a boiling point close to that of HFO-1234yf and is very difficult to separate from HFO-1234yf. These separations require very severe conditions, which are generally expensive. US 2013/0317262 notably discloses a process for purifying 2,3,3,3-tetrafluoropropene by extractive distillation to remove 3,3,3-trifluoropropene.

The present invention thus provides a simple and inexpensive process for manufacturing high-purity HFO-1234yf which does not have the abovementioned drawbacks.

SUMMARY OF THE INVENTION

According to a first aspect, the present invention relates to a process for purifying 1,1,1,2,3-pentafluoropropane comprising the steps of:

i) providing a composition A1 comprising 1,1,1,2,3-pentafluoropropane and 1,1,1,3-tetrafluoropropane;

i') optionally drying said composition A1;

ii) purifying, preferably distilling, said composition A1 under conditions that are sufficient to form at least two streams including a first stream comprising 1,1,1,2,3-pentafluoropropane and a second stream comprising 1,1,1,3-tetrafluoropropane.

According to a preferred embodiment, the mass content of 1,1,1,2,3-pentafluoropropane in said composition A1 is greater than 90%, advantageously greater than 92%, preferably greater than 94%, more preferably 96%, in particular greater than 98%, on the basis of the total weight of said composition A1.

According to a preferred embodiment, said composition A1 also comprises 1,1,1,2,3,3-hexafluoropropane, 1,1,2-trifluoroethane, 1,1,1-trifluoroethane and 1,1,1,2-tetrafluoropropane; and step ii) of said process is: ii) purification, preferably distillation, of said composition A1 under conditions that are sufficient to form a first stream comprising 1,1,1,2,3-pentafluoropropane, a second stream comprising 1,1,1,3-tetrafluoropropane and a third stream comprising 1,1,1,2,3,3-hexafluoropropane, 1,1,2-trifluoroethane, 1,1,1-trifluoroethane and 1,1,1,2-tetrafluoropropane.

According to a preferred embodiment, said composition A1 also comprises 1,1,1,2,3,3-hexafluoropropane, 1,1,2-trifluoroethane, 1,1,1-trifluoroethane and 1,1,1,2-tetrafluoropropane; and step ii) of said process is:

ii-1) distillation of said composition A1 under conditions that are sufficient to form a stream B1 comprising 1,1,1,2,3,3-hexafluoropropane, 1,1,2-trifluoroethane, 1,1,1-trifluoroethane and 1,1,1,2-tetrafluoropropane and a stream B1' comprising 1,1,1,2,3-pentafluoropropane and 1,1,1,3-tetrafluoropropane;

ii-2) distillation of said stream B1' obtained in step ii-1) to form a stream B2 comprising 1,1,1,2,3-pentafluoropropane and a stream B2' comprising 1,1,1,3-tetrafluoropropane.

Said stream B1 corresponds to said third stream comprising 1,1,1,2,3,3-hexafluoropropane, 1,1,2-trifluoroethane, 1,1,1-trifluoroethane and 1,1,1,2-tetrafluoropropane. Said stream B2 corresponds to said first stream comprising 1,1,1,2,3-pentafluoropropane. Said stream B2' corresponds to said second stream comprising 1,1,1,3-tetrafluoropropane.

According to a preferred embodiment, the mass content of 1,1,1,3-tetrafluoropropane in said first stream comprising 1,1,1,2,3-pentafluoropropane or said stream B2 is less than 5000 ppm, advantageously less than 4000 ppm, preferably less than 3000 ppm, more preferably less than 2000 ppm, in particular less than 1000 ppm, more particularly less than 500 ppm, favorably less than 375 ppm, advantageously favorably less than 250 ppm, preferably favorably less than 100 ppm, particularly favorably less than 50 ppm, more particularly favorably less than 10 ppm on the basis of the total weight of said first stream or of said stream B2.

According to a preferred embodiment, the mass content of 1,1,1,2,3,3-hexafluoropropane in said stream B1' or said stream B2 is less than 1000 ppm, advantageously less than 750 ppm, preferably less than 500 ppm, more preferably less than 250 ppm, in particular less than 100 ppm, more particularly less than 50 ppm on the basis of the total weight of said stream B1' or of said stream B2.

According to a preferred embodiment, the mass content of 1,1,1,2-tetrafluoropropane in said stream B1' or said stream B2 is less than 5000 ppm, advantageously less than 4000 ppm, preferably less than 3000 ppm, more preferably less than 2000 ppm, in particular less than 1000 ppm, more particularly less than 500 ppm, favorably less than 375 ppm, advantageously favorably less than 250 ppm, preferably favorably less than 100 ppm, particularly favorably less than 50 ppm, more particularly favorably less than 10 ppm on the basis of the total weight of said stream B1' or B2.

According to a preferred embodiment, the mass content of 1,1,2-trifluoroethane and/or 1,1,1-trifluoroethane in said stream B1' or said stream B2 is less than 50 ppm, advantageously less than 40 ppm, preferably less than 30 ppm, more preferably less than 20 ppm, in particular less than 10 ppm on the basis of the total weight of said stream B1' or of said stream B2; more particularly, said stream B1' or said stream B2 is free of 1,1,2-trifluoroethane and/or 1,1,1-trifluoroethane, i.e. a mass content of less than 1 ppm.

According to a preferred embodiment, said first stream comprising 1,1,1,2,3-pentafluoropropane or said stream B2 is subjected to a dehydrofluorination step iii) to form a stream C1 comprising 2,3,3,3-tetrafluoropropene.

According to a preferred embodiment, said stream C1 is purified under conditions that are sufficient to obtain a stream C3 comprising at least 99.5%, advantageously at least 99.8% by weight of 2,3,3,3-tetrafluoropropene on the basis of the total weight of said stream C3.

According to a preferred embodiment, the stream C3 also comprises 3,3,3-trifluoropropene and the mass content of 3,3,3-trifluoropropene in the stream C3 is less than 100 ppm, advantageously less than 75 ppm, preferably less than 50 ppm, more preferably less than 25 ppm, in particular less than 10 ppm, more particularly less than 5 ppm on the basis of the total weight of said first stream C3.

According to a preferred embodiment, the stream C3 also comprises 1,2,3,3,3-pentafluoropropene and the mass content of 1,2,3,3,3-pentafluoropropene in the stream C3 is less than 100 ppm, advantageously less than 75 ppm, preferably less than 50 ppm, more preferably less than 25 ppm, in particular less than 10 ppm on the basis of the total weight of said first stream C3.

According to a preferred embodiment, the stream C3 also comprises 1,1,2-trifluoroethane and/or 1,1,1-trifluoroethane and the mass content of 1,1,2-trifluoroethane and/or 1,1,1-trifluoroethane in the stream C3 is less than 200 ppm, advantageously less than 150 ppm, preferably less than 100 ppm, more preferably less than 75 ppm, in particular less than 50 ppm on the basis of the total weight of said first stream C3. According to a preferred embodiment, said composition A1 is obtained via a process comprising the following steps:

a) gas-phase hydrogenation of hexafluoropropene in the presence of hydrogen and of a hydrogenation catalyst to form a stream comprising 1,1,1,2,3,3-hexafluoropropane;

a') optionally, drying of said stream comprising 1,1,1,2,3,3-hexafluoropropane;

a") optionally, purification, preferably distillation, of said stream comprising 1,1,1,2,3,3-hexafluoropropane obtained from step a) or a');

b) dehydrofluorination of said stream comprising 1,1,1,2,3,3-hexafluoropropane obtained in step a) or a') or a") to form a stream comprising 1,2,3,3,3-pentafluoropropene;

b') optionally, drying of said stream comprising 1,2,3,3,3-pentafluoropropene;

b") optionally, purification, preferably distillation, of said stream comprising 1,2,3,3,3-pentafluoropropene obtained from step b) or b');

c) gas-phase hydrogenation of the 1,2,3,3,3-pentafluoropropene obtained in step b) or b') or b") in the presence of hydrogen and of a hydrogenation catalyst under conditions that are sufficient to form said composition A1.

According to a preferred embodiment, the hydrogenation catalyst used in steps a) and/or c) comprises between 0.001% and 1.0% by weight of palladium supported on alumina, preferably in the alpha polymorphic form.

According to another aspect, the present invention provides a composition comprising:

at least 99.5%, advantageously at least 99.8%, by weight of 1,1,1,2,3-pentafluoropropane, less than 500 ppm, advantageously less than 375 ppm, preferably less than 250 ppm, more preferably less than 100 ppm, in particular less than 50 ppm, more particularly less than 10 ppm of 1,1,1,3-tetrafluoropropane;

less than 1000 ppm, advantageously less than 750 ppm, preferably less than 500 ppm, more preferably less than 250 ppm, in particular less than 100 ppm, more particularly less than 50 ppm of 1,1,1,2,3,3-hexafluoropropane;

less than 50 ppm, advantageously less than 40 ppm, preferably less than 30 ppm, more preferably less than 20 ppm, in particular less than 10 ppm, more particularly less than 1 ppm of 1,1,2-trifluoroethane and/or 1,1,1-trifluoroethane;

less than 100 ppm, advantageously less than 75 ppm, preferably less than 50 ppm, more preferably less than 25 ppm, in particular less than 10 ppm, more particularly less than 1 ppm of 1,1,1,2-tetrafluoropropane; on the basis of the total weight of the composition.

According to another aspect, the present invention provides a composition comprising:
- at least 99.5%, advantageously at least 99.8%, by weight of 2,3,3,3-tetrafluoropropene,
- less than 100 ppm, advantageously less than 75 ppm, preferably less than 50 ppm, more preferably less than 25 ppm, in particular less than 10 ppm, more particularly less than 5 ppm of 3,3,3-trifluoropropene,
- less than 100 ppm, advantageously less than 75 ppm, preferably less than 50 ppm, more preferably less than 25 ppm, in particular less than 10 ppm of 1,2,3,3,3-pentafluoropropene,
- less than 200 ppm, advantageously less than 150 ppm, preferably less than 100 ppm, more preferably less than 75 ppm, in particular less than 50 ppm of 1,1,2-trifluoroethane and/or 1,1,1-trifluoroethane, and
- less than 20 ppm, advantageously less than 15 ppm, preferably less than 10 ppm, in particular less than 5 ppm of 1,1,1,2,3-pentafluoropropane, on the basis of the total weight of said composition.

DETAILED DESCRIPTION OF THE INVENTION

Figure 1A:
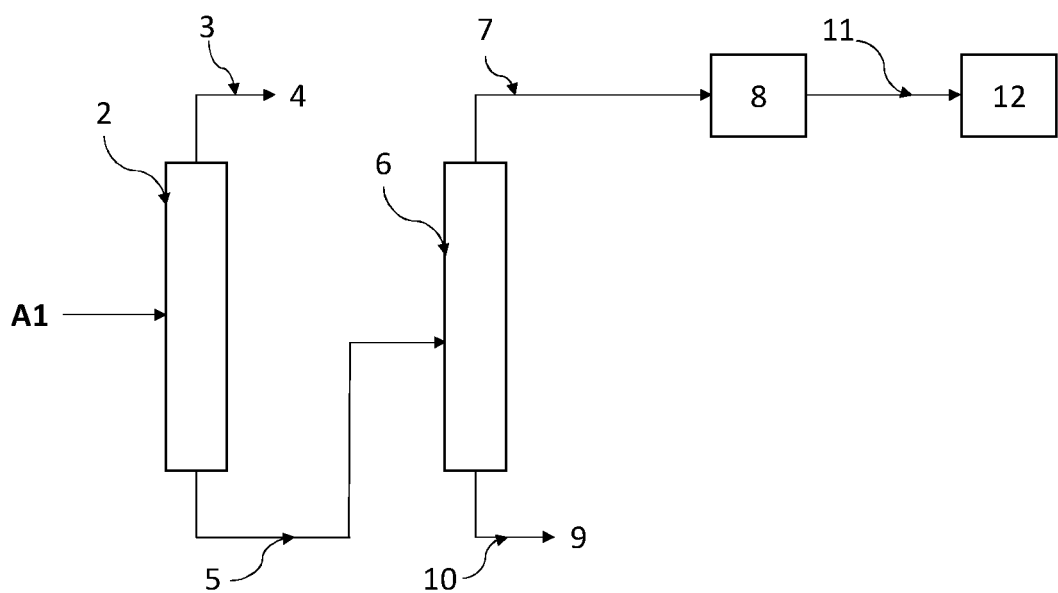
FIGS. 1a and 1b schematically represent a process for purifying 1,1,1,2,3-pentafluoropropane and for producing 2,3,3,3-tetrafluoropropene according to a particular embodiment of the present invention.

According to a first aspect, the present invention relates to a process for purifying 1,1,1,2,3-pentafluoropropane. Preferably, said purification process comprises the steps of:
i) providing a composition A1 comprising 1,1,1,2,3-pentafluoropropane and 1,1,1,3-tetrafluoropropane;
i') optionally drying said composition A1;
ii) purifying, preferably distilling, said composition A1 under conditions that are sufficient to form at least two streams including a first stream comprising 1,1,1,2,3-pentafluoropropane and a second stream comprising 1,1,1,3-tetrafluoropropane.

The purification according to step ii) of the present invention notably enables the separation of 1,1,1,2,3-pentafluoropropane from all or some of the compounds with a boiling point greater than that of 1,1,1,2,3-pentafluoropropane, preferably with a boiling point at least 5° C. greater than that of 1,1,1,2,3-pentafluoropropane.

According to a preferred embodiment, said composition A1 also comprises 1,1,1,2,3,3-hexafluoropropane, 1,1,2-trifluoroethane, 1,1,1-trifluoroethane and 1,1,1,2-tetrafluoropropane; and step ii) of said process is:
ii) purification, preferably distillation, of said composition A1 under conditions that are sufficient to form a first stream comprising 1,1,1,2,3-pentafluoropropane, a second stream comprising 1,1,1,3-tetrafluoropropane, and a third stream comprising 1,1,1,2,3,3-hexafluoropropane, 1,1,2-trifluoroethane, 1,1,1-trifluoroethane and 1,1,1,2-tetrafluoropropane.

Thus, according to a preferred embodiment, the present invention may concern a process for purifying 1,1,1,2,3-pentafluoropropane comprising the steps of:
i) providing a composition A1 comprising 1,1,1,2,3-pentafluoropropane, 1,1,1,3-tetrafluoropropane, 1,1,1,2,3,3-hexafluoropropane, 1,1,2-trifluoroethane, 1,1,1-trifluoroethane and 1,1,1,2-tetrafluoropropane;
i') optionally drying said composition A1;
ii) purifying, preferably distilling, said composition A1 under conditions that are sufficient to form a first stream comprising 1,1,1,2,3-pentafluoropropane, a second stream comprising 1,1,1,3-tetrafluoropropane, and a third stream comprising 1,1,1,2,3,3-hexafluoropropane, 1,1,2-trifluoroethane, 1,1,1-trifluoroethane and 1,1,1,2-tetrafluoropropane.

According to a particular embodiment, the purification of said composition A1 may be performed in a single step using a dividing-wall distillation column.

According to another particular embodiment, the purification of said composition A1 may be performed by implementing two successive distillation steps, via the use, for example, of two distillation columns. Thus, according to a particular embodiment, the present invention may concern a process for purifying 1,1,1,2,3-pentafluoropropane comprising the steps of:
i) providing a composition A1 comprising 1,1,1,2,3-pentafluoropropane, 1,1,1,3-tetrafluoropropane, 1,1,1,2,3,3-hexafluoropropane, 1,1,2-trifluoroethane, 1,1,1-trifluoroethane and 1,1,1,2-tetrafluoropropane;
i') optionally drying said composition A1;
ii-1) distilling said composition A1 under conditions that are sufficient to form a stream B1 comprising 1,1,1,2,3,3-hexafluoropropane, 1,1,2-trifluoroethane, 1,1,1-trifluoroethane and 1,1,1,2-tetrafluoropropane and a stream B1' comprising 1,1,1,2,3-pentafluoropropane and 1,1,1,3-tetrafluoropropane;
ii-2) distilling said stream B1' obtained in step ii-1) to form a stream B2 comprising 1,1,1,2,3-pentafluoropropane and a stream B2' comprising 1,1,1,3-tetrafluoropropane.

Said stream B2 may correspond to said first stream comprising 1,1,1,2,3-pentafluoropropane mentioned above. Said stream B2' may correspond to said second stream comprising 1,1,1,3-tetrafluoropropane mentioned above. Said stream B1 may correspond to said third stream comprising 1,1,1,2,3,3-hexafluoropropane, 1,1,2-trifluoroethane, 1,1,1-trifluoroethane and 1,1,1,2-tetrafluoropropane mentioned above.

Preferably, said drying of the composition A1 may be performed by placing said composition A1 in contact with a solid absorbent. Said solid absorbent may comprise an agent which absorbs acidic molecules and/or a water-absorbing agent. Said water-absorbing agent may be an inorganic salt such as magnesium sulfate, calcium sulfate, calcium chloride or may be molecular sieves of 3A, 4A, 5A, AW500, XH-7, XH-9 or 13X type, silica gel, active charcoal or a mixture thereof. Said agent which absorbs acidic molecules may be a metal oxide such as aluminum oxide, an alkaline-earth metal oxide, an alkali metal oxide or the hydroxide of a metal such as aluminum hydroxide, an alkaline-earth metal hydroxide, an alkali metal hydroxide, aluminosilicates such as andalusite, kyanite, sillimanite, calcium aluminosilicate, sodium aluminosilicate or silica or a mixture thereof. When the drying step is performed in the presence of a water-absorbing agent and an agent which absorbs acidic molecules, said composition A1 is preferably placed in contact with the agent which absorbs acidic molecules and then with the water-absorbing agent. The agent which absorbs acidic molecules preferably absorbs hydrofluoric acid.

Preferably, step ii-1) is performed at a pressure of between 1 and 20 bar, advantageously between 1 and 15 bar absolute, preferably between 5 and 10 bar absolute. Preferably, in step ii-1), said stream B1 is recovered at the top of the distillation column. Said stream B1' is recovered at the bottom of the distillation column Preferably, the temperature at the top of the distillation column is between 20° C. and 100° C. and preferably between 45 and 75° C.

Preferably, step ii-2) is performed at a pressure of between 1 and 20 bar, advantageously between 1 and 10 bar absolute, preferably between 3 and 6 bar absolute.

Preferably, in step ii-2), said stream B2 is recovered at the top of the distillation column. Said stream B2' is recovered at the bottom of the distillation column. Preferably, the temperature at the top of the distillation column is between 40° C. and 100° C. and preferably between 50 and 80° C.

According to a preferred embodiment, the mass content of 1,1,1,2,3-pentafluoropropane in said composition A1 is greater than 80%, advantageously greater than 90%, preferably greater than 92%, more preferably greater than 94%, in particular greater than 96%, more particularly greater than 98% on the basis of the total weight of said composition A1.

The mass content of 1,1,1,3-tetrafluoropropane in said composition A1 and/or said stream B1' may be less than 5%, advantageously less than 4%, preferably less than 3%, more preferably less than 2%, in particular less than 1%, more particularly less than 0.5% on the basis of the total weight of said composition A1 and/or said stream B1'.

Preferably, the mass content of 1,1,1,3-tetrafluoropropane in said composition A1 and/or said stream B1' is less than 3000 ppm on the basis of the total weight of said composition A1 and/or said stream B1', advantageously less than 2500 ppm, preferably less than 2000 ppm, in particular less than 1500 ppm, more particularly less than 1000 ppm on the basis of the total weight of said composition A1 and/or said stream B1'.

According to a preferred embodiment, as mentioned above, said stream A1 may also comprise 1,1,1,2,3,3-hexafluoropropane, 1,1,2-trifluoroethane, 1,1,1-trifluoroethane and 1,1,1,2-tetrafluoropropane.

Thus, when it contains any, the mass content of 1,1,1,2,3,3-hexafluoropropane in said composition A1 may be less than 1000 ppm on the basis of the total weight of said composition A1, advantageously less than 750 ppm, preferably less than 500 ppm, in particular less than 375 ppm, more particularly less than 250 ppm. The mass content of 1,1,1,2,3-hexafluoropropane in said composition A1 may be greater than 20 ppm, advantageously greater than 30 ppm, in particular greater than 60 ppm.

When it contains any, the mass content of 1,1,2-trifluoroethane and/or 1,1,1-trifluoroethane in said composition A1 may be less than 5% on the basis of the total weight of said composition A1, advantageously less than 4%, preferably less than 3%, in particular less than 2%, more particularly less than 1%.

When it contains any, the mass content of 1,1,1,2-tetrafluoropropane in said composition A1 may be less than 15% on the basis of the total weight of said composition A1, advantageously less than 10%, preferably less than 5%, in particular less than 2%, more particularly less than 1%.

Step ii) or ii-1) and ii-2) of purification of said composition A1 according to the present purification process enables production of said first stream comprising 1,1,1,2,3-pentafluoropropane or said stream B2 with a purity greater than that of said composition A1. Thus, the mass content of 1,1,1,3-tetrafluoropropane in said composition A1 is preferably greater than that obtained in said first stream or said stream B2 following the implementation of step ii) or ii-1) and ii-2).

Preferably, the mass content of 1,1,1,2,3-pentafluoropropane in said first stream comprising 1,1,1,2,3-pentafluoropropane or said stream B2 is at least 99.5%, advantageously at least 99.8%, by weight on the basis of the total weight of said first stream or of said stream B2.

Advantageously, the mass content of 1,1,1,3-tetrafluoropropane in said first stream comprising 1,1,1,2,3-pentafluoropropane or said stream B2 is less than 500 ppm, advantageously less than 375 ppm, preferably less than 250 ppm, more preferably less than 100 ppm, in particular less than 50 ppm, more particularly less than 10 ppm on the basis of the total weight of said first stream or of said stream B2.

Preferably, when it contains any, the mass content of 1,1,1,2,3,3-hexafluoropropane in said stream B1' or said stream B2 is less than 1000 ppm, advantageously less than 750 ppm, preferably less than 500 ppm, more preferably less than 250 ppm, in particular less than 100 ppm, more particularly less than 50 ppm on the basis of the total weight of said stream B1' or of said stream B2.

Preferably, when it contains any, the mass content of 1,1,2-trifluoroethane and/or 1,1,1-trifluoroethane in said stream B1' or said stream B2 is less than 50 ppm, advantageously less than 40 ppm, preferably less than 30 ppm, more preferably less than 20 ppm, in particular less than 10 ppm on the basis of the total weight of said stream B1' or of said stream B2; more particularly, said stream B1' or said stream B2 is free of 1,1,2-trifluoroethane, i.e. a mass content of less than 1 ppm.

Preferably, when it contains any, the mass content of 1,1,1,2-tetrafluoropropane in said stream B1' or said stream B2 is less than 100 ppm, advantageously less than 75 ppm, preferably less than 50 ppm, more preferably less than 25 ppm, in particular less than 10 ppm on the basis of the total weight of said stream B1' or of said stream B2; more particularly, said stream B1' or said stream B2 is free of 1,1,1,2-tetrafluoropropane, i.e. a mass content of less than 1 ppm.

The stream A1, B1' and/or B2 may also comprise 1,2,3,3,3-pentafluoropropene. Preferably, when it contains any, the mass content of 1,2,3,3,3-pentafluoropropene in said stream B1' or said stream B2 is less than 200 ppm, advantageously less than 150 ppm, preferably less than 100 ppm, more preferably less than 50 ppm, in particular less than 10 ppm on the basis of the total weight of said stream B1' or of said stream B2. Preferably, the mass content of 1,2,3,3,3-pentafluoropropene in said stream A1 is less than 10%, advantageously less than 5%, preferably less than 1%, more preferably less than 5000 ppm, in particular less than 2000 ppm on the basis of the total weight of said stream A1.

The stream A1, B1' and/or B2 may also comprise hydrogen fluoride (HF). Preferably, when it contains any, the mass content of HF in said stream B1' or said stream B2 is less than 2000 ppm, advantageously less than 1500 ppm, preferably less than 1000 ppm, more preferably less than 500 ppm, in particular less than 100 ppm on the basis of the total weight of said stream B1' or of said stream B2. Preferably, the mass content of HF in said stream A1 is less than 1%, advantageously less than 7500 ppm, preferably less than 5000 ppm, more preferably less than 2500 ppm on the basis of the total weight of said stream A1.

The stream A1, B1' and/or B2 may also comprise water ($H_2O$). When it contains any, the mass content of water in said stream B1' or said stream B2 is less than 1000 ppm, preferably less than 750 ppm, more preferably less than 500 ppm, in particular less than 250 ppm on the basis of the total weight of said stream B1' or of said stream B2. When it contains any, the mass content of water in said stream A1 is less than 10000 ppm, advantageously less than 5000 ppm, preferably less than 2500 ppm on the basis of the total weight of said stream A1.

Said second stream or said stream B2' obtained at the bottom of the distillation column during step ii) or ii-2) may be recovered to be subsequently upgraded or may be evacuated to an incineration device. In addition, said stream B1 obtained in step ii-1) or said third stream obtained in step ii) may be recovered to be subsequently upgraded or may be evacuated to an incineration device.

The present purification process enables the removal of the precursors of impurities that are difficult to separate from 2,3,3,3-tetrafluoropropene upstream of the reaction in which they are formed. For example, 3,3,3-trifluoropropene is difficult to separate from 2,3,3,3-tetrafluoropropene. The Applicant has identified that 3,3,3-trifluoropropene can be formed from precursors such as 1,1,1,3-tetrafluoropropane and/or 1,1,1,2-tetrafluoropropane. Thus, via the present purification process, a stream of 1,1,1,2,3-pentafluoropropane is obtained in which the content of 1,1,1,3-tetrafluoropropane is reduced. According to a particular embodiment of the present purification process, a stream of 1,1,1,2,3-pentafluoropropane is obtained in which the contents of 1,1,1,3-tetrafluoropropane, 1,1,1,2,3,3-hexafluoropropane, 1,1,2-trifluoroethane, 1,1,1-trifluoroethane and 1,1,1,2-tetrafluoropropane are reduced. This makes it possible to reduce the impurities such as 1,2,3,3,3-pentafluoropropene or 3,3,3-trifluoropropene in 2,3,3,3-tetrafluoropropene.

According to a preferred embodiment, said first stream comprising 1,1,1,2,3-pentafluoropropane or said stream B2 is subjected to a dehydrofluorination step iii) to form a stream C1 comprising 2,3,3,3-tetrafluoropropene.

Thus, according to a second aspect of the present invention, a process for producing 2,3,3,3-tetrafluoropropene is provided. Said process for producing 2,3,3,3-tetrafluoropropene comprises the steps of:
  i) providing a composition A1 comprising 1,1,1,2,3-pentafluoropropane and 1,1,1,3-tetrafluoropropane;
  i') optionally drying said composition A1;
  ii) purifying, preferably distilling, said composition A1 under conditions that are sufficient to form at least two streams including a first stream comprising 1,1,1,2,3-pentafluoropropane and a second stream comprising 1,1,1,3-tetrafluoropropane;
  iii) dehydrofluorination of said first stream comprising 1,1,1,2,3-pentafluoropropane to form a stream C1 comprising 2,3,3,3-tetrafluoropropene.

According to a preferred embodiment, said process for producing 2,3,3,3-tetrafluoropropene comprises the steps of:
  i) providing a composition A1 comprising 1,1,1,2,3-pentafluoropropane, 1,1,1,3-tetrafluoropropane, 1,1,1,2,3,3-hexafluoropropane, 1,1,2-trifluoroethane, 1,1,1-trifluoroethane and 1,1,1,2-tetrafluoropropane;
  i') optionally drying said composition A1;
  ii) purifying, preferably distilling, said composition A1 under conditions that are sufficient to form a first stream comprising 1,1,1,2,3-pentafluoropropane, a second stream comprising 1,1,1,3-tetrafluoropropane, and a third stream comprising 1,1,1,2,3,3-hexafluoropropane, 1,1,2-trifluoroethane, 1,1,1-trifluoroethane and 1,1,1,2-tetrafluoropropane;
  iii) dehydrofluorination of said first stream comprising 1,1,1,2,3-pentafluoropropane to form a stream C1 comprising 2,3,3,3-tetrafluoropropene.

According to a particular embodiment, said process for producing 2,3,3,3-tetrafluoropropene comprises the steps of:
  i) providing a composition A1 comprising 1,1,1,2,3-pentafluoropropane, 1,1,1,3-tetrafluoropropane, 1,1,1,2,3,3-hexafluoropropane, 1,1,2-trifluoroethane, 1,1,1-trifluoroethane and 1,1,1,2-tetrafluoropropane;
  i') optionally drying said composition A1;
  ii-1) distilling said composition A1 under conditions that are sufficient to form a stream B1 comprising 1,1,1,2,3,3-hexafluoropropane, 1,1,2-trifluoroethane, 1,1,1-trifluoroethane and 1,1,1,2-tetrafluoropropane and a stream B1' comprising 1,1,1,2,3-pentafluoropropane and 1,1,1,3-tetrafluoropropane;
  ii-2) distilling said stream B1' obtained in step ii-1) to form a stream B2 comprising 1,1,1,2,3-pentafluoropropane and a stream B2' comprising 1,1,1,3-tetrafluoropropane;
  iii) dehydrofluorination of said stream B2 comprising 1,1,1,2,3-pentafluoropropane to form a stream C1 comprising 2,3,3,3-tetrafluoropropene.

The dehydrofluorination step may be performed according to the techniques known to those skilled in the art as described, for example, in WO 2011/010025, page 10, lines 1-21 and page 14, line 19 to page 15, line 4, which is incorporated herein by reference. For example, potassium hydroxide is preferably present in the reaction medium in an amount of between 20% and 75% by weight and advantageously between 55% and 70% by weight relative to the weight of the mixture of water and KOH. For example, the aqueous reaction medium of the dehydrofluorination step, comprising KOH, is preferably maintained at a temperature of between 80 and 180° C., advantageously between 125 and 180° C.

Said stream C1 may also comprise, besides 2,3,3,3-tetrafluoropropene, one or more of the compounds selected from the group consisting of 3,3,3-trifluoropropene, 1,2,3,3,3-pentafluoropropene, 1,1,2-trifluoroethane, 1,1,1-trifluoroethane and 1,2-difluoroethylene and 1,1-difluoroethylene. These compounds may be derived from side reactions taking place during said step iii) according to the present invention, this possibly being due to the presence of residual impurities, other than 1,1,1,3-tetrafluoropropane, in the composition A1 or said first stream or said stream B2.

Preferably, the mass content of 3,3,3-trifluoropropene in the stream C1 is less than 100 ppm, advantageously less than 75 ppm, preferably less than 50 ppm, more preferably less than 25 ppm on the basis of the total weight of said stream C1. This content of 3,3,3-trifluoropropene in said stream C1 may be obtained by means of performing the step ii) or steps ii-1) and ii-2), of purification, preferably distillation, of said composition A1 notably comprising 1,1,1,2,3-pentafluoropropane and 1,1,1,3-tetrafluoropropane. The separation between 1,1,1,2,3-pentafluoropropane and 1,1,1,3-tetrafluoropropane, prior to the dehydrofluorination of 1,1,1,2,3-pentafluoropropane (step iii) of the present process) makes it possible finally to obtain a high-purity stream C1, virtually free of 3,3,3-trifluoropropene. The separation between 1,1,1,2,3-pentafluoropropane, on the one hand, and 1,1,1,2,3,3-hexafluoropropane, 1,1,2-trifluoroethane, 1,1,1-trifluoroethane and 1,1,1,2-tetrafluoropropane, on the other hand, if the latter compounds are present in said composition A1, prior to the dehydrofluorination of 1,1,1,2,3-pentafluoropropane (step iii) of the present process) makes it possible finally to obtain a high-purity stream C1 virtually free of 1,2,3,3,3-pentafluoropropene and/or of 3,3,3-trifluoropropene.

According to a preferred embodiment, said stream C1 is purified under conditions that are sufficient to obtain a stream C3 comprising at least 99.5% by weight, preferably at least 99.8% by weight of 2,3,3,3-tetrafluoropropene on the basis of the total weight of said stream C3.

Said stream C1 may thus be purified by means of one or more steps including, for example, condensation, evaporation, decantation, absorption, washing, liquid-liquid extraction, photochlorination, distillation, for example extractive distillation, azeotropic distillation, adsorption on solid and more particularly adsorption on a molecular sieve, alumina or active charcoal, and membrane separation. The purification of said stream C1 may comprise at least one step of adsorption, preferably on activated alumina and/or a molecular sieve and at least one distillation step.

Thus, the present process for producing 2,3,3,3-tetrafluoropropene may comprise a step iv) of purifying the stream C1 obtained in step iii) to form said stream C3.

In particular, said step iv) of purifying said stream C1 comprises a first distillation to separate the 2,3,3,3-tetrafluoropropene from the light impurities and a second distillation to separate the 2,3,3,3-tetrafluoropropene from the heavy impurities, notably 1,1,1,2,3-pentafluoropropane.

In particular, the present process for producing 2,3,3,3-tetrafluoropropene may comprise the following steps:

iv-1) purification, preferably distillation, of said stream C1 obtained in step iii) to form a stream C2, preferably at the top of the distillation column, and a stream CT, preferably at the bottom of the distillation column, comprising 2,3,3,3-tetrafluoropropene;

iv-2) purification, preferably distillation, of said stream C2' obtained in step iv-1) to form said stream C3, preferably at the top of the distillation column, comprising 2,3,3,3-tetrafluoropropene, and a stream C3', preferably at the bottom of the distillation column, comprising 1,1,1,2,3-pentafluoropropane.

Said step iv-1) may be performed at a pressure of from 2 to 20 bar, advantageously from 11 to 15 bar absolute. Preferably, the temperature at the top of the distillation column is from 35° C. to 50° C. The stream C2 may notably contain 1,1-difluoroethylene.

Said step iv-2) may be performed at a pressure of from 2 to 20 bar, advantageously from 9 to 13 bar absolute. Preferably, the temperature at the top of the distillation column is from 36° C. to 51° C.

Preferably, said stream C3' may be recycled into step iii) or into step i). Preferably, the mass content of 1,2,3,3,3-pentafluoropropene in said stream C1 is less than 100 ppm, advantageously less than 75 ppm, preferably less than 50 ppm, in particular less than 25 ppm on the basis of the total weight of said stream C1.

Preferably, the mass content of 1,1,1,2,3-pentafluoropropene in said stream C1 or said stream C2' is less than 40%, advantageously less than 30%, preferably less than 20%, in particular less than 10% on the basis of the total weight of said stream C1 or said stream C2'.

Preferably, the mass content of 1,2-difluoroethylene in said stream CT and/or said stream C3 is less than 500 ppm, advantageously less than 250 ppm, preferably less than 100 ppm, in particular less than 50 ppm on the basis of the total weight of said stream C2' or said stream C3.

As mentioned above, the purification of said stream C1 enables the production of a stream C3 comprising purified 2,3,3,3-tetrafluoropropene.

Preferably, the mass content of 3,3,3-trifluoropropene in the stream C3 is less than 100 ppm, advantageously less than 75 ppm, preferably less than 50 ppm, more preferably less than 25 ppm, in particular less than 10 ppm, more particularly less than 5 ppm on the basis of the total weight of said stream C3.

Preferably, the mass content of 1,2,3,3,3-pentafluoropropene in said stream C3 is less than 100 ppm, advantageously less than 75 ppm, preferably less than 50 ppm, more preferably less than 25 ppm, in particular less than 10 ppm on the basis of the total weight of said stream C3.

According to a preferred embodiment, the stream C3 also comprises 1,1,2-trifluoroethane and/or 1,1,1-trifluoroethane and the mass content of 1,1,2-trifluoroethane and/or 1,1,1-trifluoroethane in the stream C3 is less than 200 ppm, advantageously less than 150 ppm, preferably less than 100 ppm, more preferably less than 75 ppm, in particular less than 50 ppm on the basis of the total weight of said first stream C3.

Preferably, the mass content of 1,1,1,2,3-pentafluoropropane in said stream C3 is less than 10 ppm, advantageously less than 5 ppm on the basis of the total weight of said stream C3; preferably, said stream C3 is free of 1,1,1,2,3-pentafluoropropane, i.e. a mass content of less than 1 ppm.

According to a preferred embodiment, said composition A1 is obtained via a process comprising the following steps:

a) gas-phase hydrogenation of hexafluoropropene in the presence of hydrogen and of a hydrogenation catalyst to form a stream comprising 1,1,1,2,3,3-hexafluoropropane;

a') optionally, drying of said stream comprising 1,1,1,2,3,3-hexafluoropropane;

a") optionally, purification, preferably distillation, of said stream comprising 1,1,1,2,3,3-hexafluoropropane obtained from step a) or a');

b) dehydrofluorination of said stream comprising 1,1,1,2,3,3-hexafluoropropane obtained in step a) or a') or a") to form a stream comprising 1,2,3,3,3-pentafluoropropene;

b') optionally, drying of said stream comprising 1,2,3,3,3-pentafluoropropene;

b") optionally, purification, preferably distillation, of said stream comprising 1,2,3,3,3-pentafluoropropene obtained from step b) or b');

c) gas-phase hydrogenation of the 1,2,3,3,3-pentafluoropropene obtained in step b) or b') or b") in the presence of hydrogen and of a hydrogenation catalyst under conditions that are sufficient to form said composition A1.

Preferably, the hydrogenation step a) and/or c) is performed in the presence of a catalyst. Catalysts that may notably be mentioned include metals such as Pd, Ru, Pt, Rh, Ir, Fe, Co, Ni, Cu, Ag, Re, Os, Au, Ge, Te, optionally supported. Supports that may notably be mentioned include carbon, alumina, fluorinated alumina, $AlF_3$, oxides, oxyfluorides and fluorides of Cr, Ti, Zr, Mg, Zn, silica and silicon carbide. The amount of metals present in the catalyst, when it is supported, may be between 0.001% and 10% by weight, preferably between 0.001% and 1.0% by weight, in particular from 0.01% to 0.2% by weight. The hydrogenation step is advantageously performed in the presence of Pd supported on alumina, preferably in the alpha polymorphic form. In particular, said hydrogenation catalyst may comprise Pd supported on alumina in the alpha polymorphic form; palladium representing between 0.001% and 1.0% by weight, preferably from 0.01% to 0.2% on the basis of the total weight of the catalyst. The hydrogenation step may be performed either in the liquid phase or in the gas phase. The gas phase is, however, preferred.

The hydrogenation step a) is performed in the presence of hydrogen, advantageously with a hydrogen/hexafluoropropene mole ratio of between 1 and 50 and most particularly between 2 and 15. The hydrogenation step c) is performed in the presence of hydrogen, advantageously with a hydrogen/1,2,3,3,3-pentafluoropropene mole ratio of between 1 and 50 and most particularly between 2 and 15.

The hydrogenation step a) and/or c) is preferably performed at a temperature of between 50 and 200° C., preferably between 80 and 120° C. Preferably, the temperature at the inlet of the reactor of the hydrogenation step a) and/or c) is between 30 and 100° C., advantageously between 40 and 80° C.

The contact time of the hydrogenation step a) and/or c), defined as the ratio of the volume of the catalytic bed to the volume flow rate of the total stream under normal temperature and pressure conditions, is preferably between 0.1 s and 20 s and advantageously between 0.5 and 5 s.

The hydrogenation step a) and/or c) is preferably performed at an absolute pressure of between 0.5 and 20 bar and advantageously between 1 and 5 bar.

Preferably, the hydrogenation step a) and/or c) is performed in the presence of a diluent which may be co-introduced with the reagents into the reaction medium. The diluent is an inert gas which does not react under the conditions of the hydrogenation step. Nitrogen, helium or argon may be mentioned as diluent. The mole ratio of the diluent/reagents at the inlet of the reactor of the hydrogenation step a) and/or c) may be between 100:1 and 1:1, preferably between 10:1 and 1:1, advantageously between 5:1 and 1:1.

In particular, during step a) according to the present invention, the diluent may be the hydrogenation product which is HFC-236ea. In this case, one part of the gaseous effluent obtained from the reactor comprising HFC-236ea, unreacted hydrogen and optionally unreacted hexafluoropropene, 1,1,1,2,3-pentafluoropropane (HFC-245eb) and 1,1,1,2-tetrafluoropropane (HFC-254eb) is recycled and the other part of the gaseous effluent obtained from the reactor is subjected to a separation and/or purification step. The gas stream comprising the recycling loop and the reagents may be preheated before introduction into the reactor. The portion of the gaseous effluent recycled into the reactor preferably represents at least 90% by volume of the total amount of effluent at the reactor outlet, advantageously at least 93% by volume. Particularly preferably, the portion of the effluent recycled into the reactor represents between 94% and 98% by volume of the total effluent at the reactor outlet.

The stream on conclusion of the hydrogenation step a) may be subjected to a condensation step under conditions such that the unreacted hydrogen is not condensed and such that part of HFC-236a formed in step a) is condensed. Preferably, the condensation step is performed at a temperature of between 0 and 50° C. and at a pressure of between 0.5 and 20 bar absolute, advantageously between 1 and 5 bar absolute. Preferably, the condensation step is performed under conditions such that between 1% and 30% of HFC-236ea leaving the reactor is condensed and advantageously between 2% and 10% is condensed. The uncondensed fraction is then recycled into the hydrogenation step a) after optional heating. The condensed fraction is then evaporated before being sent into step b). Before performing step b), the condensed fraction may be purified and/or dried.

If it is performed, step a') of drying said stream comprising 1,1,1,2,3,3-hexafluoropropane may be performed by placing said stream in contact with a solid absorbent. Said solid absorbent may comprise an agent which absorbs acidic molecules and/or a water-absorbing agent. Said water-absorbing agent may be an inorganic salt such as magnesium sulfate, calcium sulfate, calcium chloride or may be a molecular sieve of 3A, 4A, 5A, AW500, XH-7, XH-9 or 13X type, silica gel, active charcoal or a mixture thereof. Said agent which absorbs acidic molecules may be a metal oxide such as aluminum oxide, an alkaline-earth metal oxide, an alkali metal oxide or the hydroxide of a metal such as aluminum hydroxide, an alkaline-earth metal hydroxide, an alkali metal hydroxide, aluminosilicates such as andalusite, kyanite, sillimanite, calcium aluminosilicate, sodium aluminosilicate or silica or a mixture thereof. When the drying step is performed in the presence of a water-absorbing agent and an agent which absorbs acidic molecules, said stream is preferably placed in contact with the agent which absorbs acidic molecules and then with the water-absorbing agent. The agent which absorbs acidic molecules preferably absorbs hydrofluoric acid.

If it is performed, step a") of purification, preferably distillation, of said stream comprising 1,1,1,2,3,3-hexafluoropropane obtained from step a) or a') enables the removal of byproducts formed during step a) to recover a stream comprising purified 1,1,1,2,3,3-hexafluoropropane, i.e. in which the content of byproducts is reduced.

Step b) of dehydrofluorination of the 1,1,1,2,3,3-hexafluoropropane is performed under the conditions as detailed above in relation with step iii) of the present process. Step b) of the present process enables the production of a stream comprising 1,2,3,3,3-pentafluoropropene. This product may optionally be purified or not before performing the hydrogenation step c) described above.

According to the process of the invention, one or more adiabatic reactors are preferably used.

Thus, according to a particular aspect of the present invention, the process for producing 2,3,3,3-tetrafluoropropene comprises the following steps:

a) gas-phase hydrogenation of hexafluoropropene in the presence of hydrogen and of a hydrogenation catalyst to form a stream comprising 1,1,1,2,3,3-hexafluoropropane;

a') optionally, drying of said stream comprising 1,1,1,2,3,3-hexafluoropropane;

a") optionally, purification, preferably distillation, of said stream comprising 1,1,1,2,3,3-hexafluoropropane obtained from step a) or a');

b) dehydrofluorination of said stream comprising 1,1,1,2,3,3-hexafluoropropane obtained in step a) or a') or a") to form a stream comprising 1,2,3,3,3-pentafluoropropene;

b') optionally, drying of said stream comprising 1,2,3,3,3-pentafluoropropene;

b") optionally, purification, preferably distillation, of said stream comprising 1,2,3,3,3-pentafluoropropene obtained from step b) or b');

c) gas-phase hydrogenation of the 1,2,3,3,3-pentafluoropropene obtained in step b) or b') or b") in the presence of hydrogen and of a hydrogenation catalyst under conditions that are sufficient to form said composition A1 comprising 1,1,1,2,3-pentafluoropropane and 1,1,1,3-tetrafluoropropane;

d) purification, preferably distillation, of said composition A1 obtained in step c) under conditions that are sufficient to form at least two streams including a first stream comprising 1,1,1,2,3-pentafluoropropane and a second stream comprising 1,1,1,3-tetrafluoropropane;

e) dehydrofluorination of said first stream comprising 1,1,1,2,3-pentafluoropropane to form a stream C1 comprising 2,3,3,3-tetrafluoropropene;

e') optionally, drying of said stream C1 obtained from step e);

e") optionally, purification, preferably distillation, of said stream C1 obtained from step e) or e') under conditions that are sufficient to obtain a stream C3 comprising at least 99.5% by weight of 2,3,3,3-tetrafluoropropene on the basis of the total weight of said stream C3.

Preferably, the process for producing 2,3,3,3-tetrafluoropropene comprises the following steps:

a) gas-phase hydrogenation of hexafluoropropene in the presence of hydrogen and of a hydrogenation catalyst to form a stream comprising 1,1,1,2,3,3-hexafluoropropane;

a') optionally, drying of said stream comprising 1,1,1,2,3,3-hexafluoropropane;

a") optionally, purification, preferably distillation, of said stream comprising 1,1,1,2,3,3-hexafluoropropane obtained from step a) or a');

b) dehydrofluorination of said stream comprising 1,1,1,2,3,3-hexafluoropropane obtained in step a) or a') or a") to form a stream comprising 1,2,3,3,3-pentafluoropropene;

b') optionally, drying of said stream comprising 1,2,3,3,3-pentafluoropropene;

b") optionally, purification, preferably distillation, of said stream comprising 1,2,3,3,3-pentafluoropropene obtained from step b) or b');

c) gas-phase hydrogenation of the 1,2,3,3,3-pentafluoropropene obtained in step b) or b') or b") in the presence of hydrogen and of a hydrogenation catalyst under conditions that are sufficient to form said composition A1 comprising 1,1,1,2,3-pentafluoropropane, 1,1,1,3-tetrafluoropropane, 1,1,1,2,3,3-hexafluoropropane, 1,1,2-trifluoroethane, 1,1,1-trifluoroethane and 1,1,1,2-tetrafluoropropane;

d) purification, preferably distillation, of said composition A1 under conditions that are sufficient to form a first stream comprising 1,1,1,2,3-pentafluoropropane, a second stream comprising 1,1,1,3-tetrafluoropropane, and a third stream comprising 1,1,1,2,3,3-hexafluoropropane, 1,1,2-trifluoroethane, 1,1,1-trifluoroethane and 1,1,1,2-tetrafluoropropane;

e) dehydrofluorination of said first stream comprising 1,1,1,2,3-pentafluoropropane to form a stream C1 comprising 2,3,3,3-tetrafluoropropene;

e') optionally, drying of said stream C1 obtained from step e);

e") optionally, purification, preferably distillation, of said stream C1 obtained from step e) or e') under conditions that are sufficient to obtain a stream C3 comprising at least 99.5% by weight of 2,3,3,3-tetrafluoropropene on the basis of the total weight of said stream C3.

In particular, the process for producing 2,3,3,3-tetrafluoropropene comprises the following steps:

a) gas-phase hydrogenation of hexafluoropropene in the presence of hydrogen and of a hydrogenation catalyst to form a stream comprising 1,1,1,2,3,3-hexafluoropropane;

a') optionally, drying of said stream comprising 1,1,1,2,3,3-hexafluoropropane;

a") optionally, purification, preferably distillation, of said stream comprising 1,1,1,2,3,3-hexafluoropropane obtained from step a) or a');

b) dehydrofluorination of said stream comprising 1,1,1,2,3,3-hexafluoropropane obtained in step a) or a') or a") to form a stream comprising 1,2,3,3,3-pentafluoropropene;

b') optionally, drying of said stream comprising 1,2,3,3,3-pentafluoropropene;

b") optionally, purification, preferably distillation, of said stream comprising 1,2,3,3,3-pentafluoropropene obtained from step b) or b');

c) gas-phase hydrogenation of the 1,2,3,3,3-pentafluoropropene obtained in step b) or b') or b") in the presence of hydrogen and of a hydrogenation catalyst under conditions that are sufficient to form said composition A1 comprising 1,1,1,2,3-pentafluoropropane, 1,1,1,3-tetrafluoropropane 1,1,1,2,3,3-hexafluoropropane, 1,1,2-trifluoroethane, 1,1,1-trifluoroethane and 1,1,1,2-tetrafluoropropane;

d-1) distillation of said composition A1 under conditions that are sufficient to form a stream B1 comprising 1,1,1,2,3,3-hexafluoropropane, 1,1,2-trifluoroethane, 1,1,1-trifluoroethane and 1,1,1,2-tetrafluoropropane and a stream B1' comprising 1,1,1,2,3-pentafluoropropane and 1,1,1,3-tetrafluoropropane;

d-2) distillation of said stream B1' obtained in step ii-1) to form a stream B2 comprising 1,1,1,2,3-pentafluoropropane and a stream B2' comprising 1,1,1,3-tetrafluoropropane;

e) dehydrofluorination of said stream B2 comprising 1,1,1,2,3-pentafluoropropane to form a stream C1 comprising 2,3,3,3-tetrafluoropropene;

e') optionally, drying of said stream C1 obtained from step e);

e") optionally, purification, preferably distillation, of said stream C1 obtained from step e) or e') under conditions that are sufficient to obtain a stream C3 comprising at least 99.5% by weight of 2,3,3,3-tetrafluoropropene on the basis of the total weight of said stream C3.

Step d), step d-1), step d-2) and step e) mentioned above correspond, respectively, to step ii), step ii-1), step ii-2) and step iii) described above in the present application in relation to the process for purifying 1,1,1,2,3-pentafluoropropane and the process for producing 2,3,3,3-tetrafluoropropene.

Step b") may be performed to purify the 1,2,3,3,3-pentafluoropropene obtained in step b) or b'). The stream comprising 1,2,3,3,3-pentafluoropropene formed in step b) or b') may notably comprise 1,1,1,2,3,3-hexafluoropropane and 1,1,2-trifluoroethylene. Step b") may thus comprise a step of purification, preferably of distillation, of said stream comprising 1,2,3,3,3-pentafluoropropene to form a stream D1 comprising 1,2,3,3,3-pentafluoropropene and 1,1,2-trifluoroethylene, advantageously at the top of the distillation column; and a stream D2 comprising 1,1,1,2,3,3-hexafluoropropane, advantageously at the bottom of the distillation column.

Alternatively, step b") may comprise a step of purification, preferably of distillation, of said stream comprising 1,2,3,3,3-pentafluoropropene to form and to recover, advantageously at the top of the distillation column, a stream D3 comprising 1,1,2-trifluoroethylene and a stream D3' comprising 1,2,3,3,3-pentafluoropropene and 1,1,1,2,3,3-hexafluoropropane, advantageously at the bottom of the distillation column. Said distillation may be performed at a pressure of from 11 to 15 bara and the distillation column head temperature is from 45° C. to 65° C. Said stream D3' may be distilled to form and to recover a stream D4 comprising 1,2,3,3,3-pentafluoropropene, advantageously at the top of the distillation column, and a stream D4' comprising 1,1,1,2,3,3-hexafluoropropane, advantageously at the bottom of the distillation column Said distillation may be performed at a pressure of from 9 to 13 bara and the distillation column head temperature is from 44° C. to 60° C.

The stream D1 or D4 may be used in step c) of the present process. The stream D4' comprising 1,1,1,2,3,3-hexafluoropropane may be recycled into step b). The stream D3 may be upgraded or incinerated.

According to another aspect of the present invention, a composition is provided. Preferably, said composition comprises:

at least 99.5%, advantageously at least 99.8%, by weight of 1,1,1,2,3-pentafluoropropane, less than 500 ppm, advantageously less than 375 ppm, preferably less than 250 ppm, more preferably less than 100 ppm, in particular less than 50 ppm, more particularly less than 10 ppm of 1,1,1,3-tetrafluoropropane;

less than 1000 ppm, advantageously less than 750 ppm, preferably less than 500 ppm, more preferably less than 250 ppm, in particular less than 100 ppm, more particularly less than 50 ppm of 1,1,1,2,3,3-hexafluoropropane;

less than 50 ppm, advantageously less than 40 ppm, preferably less than 30 ppm, more preferably less than 20 ppm, in particular less than 10 ppm, more particularly less than 1 ppm of 1,1,2-trifluoroethane and/or 1,1,1-trifluoroethane;

less than 100 ppm, advantageously less than 75 ppm, preferably less than 50 ppm, more preferably less than 25 ppm, in particular less than 10 ppm, more particularly less than 1 ppm of 1,1,1,2-tetrafluoropropane;

optionally less than 200 ppm, advantageously less than 150 ppm, preferably less than 100 ppm, more preferably less than 50 ppm, in particular less than 10 ppm of 1,2,3,3,3-pentafluoropropene;

optionally less than 2000 ppm, advantageously less than 1500 ppm, preferably less than 1000 ppm, more preferably less than 500 ppm, in particular less than 100 ppm of HF;

on the basis of the total weight of the composition.

Advantageously, said composition comprises at least 99.5%, advantageously at least 99.8%, by weight of 1,1,1,2,3-pentafluoropropane.

Preferably, said composition comprises 1,1,1,2,3-pentafluoropropane and 1,1,1,3-tetrafluoropropane, and the mass content of 1,1,1,2,3-pentafluoropropane in said composition is at least 99.5%, advantageously at least 99.8%; and the mass content of 1,1,1,3-tetrafluoropropane in said composition is less than 500 ppm, advantageously less than 375 ppm, preferably less than 250 ppm, more preferably less than 100 ppm, in particular less than 50 ppm, more particularly less than 10 ppm. Preferably, the content of 1,1,1,3-tetrafluoropropane is greater than 1 ppb.

Preferably, said composition comprises 1,1,1,2,3-pentafluoropropane and 1,1,1,2,3,3-hexafluoropropane, and the mass content of 1,1,1,2,3-pentafluoropropane in said composition is at least 99.5%, advantageously at least 99.8%; and the mass content of 1,1,1,2,3,3-hexafluoropropane in said composition is less than 1000 ppm, advantageously less than 750 ppm, preferably less than 500 ppm, more preferably less than 250 ppm, in particular less than 100 ppm, more particularly less than 50 ppm. Preferably, the content of 1,1,1,2,3,3-hexafluoropropane is greater than 1 ppb.

Said composition may comprise 1,1,1,2,3-pentafluoropropane, 1,1,1,3-tetrafluoropropane and 1,1,1,2,3,3-hexafluoropropane; the mass content of 1,1,1,2,3-pentafluoropropane in said composition is at least 99.5%, advantageously at least 99.8%; the mass content of 1,1,1,2,3,3-hexafluoropropane in said composition is less than 1000 ppm, advantageously less than 750 ppm, preferably less than 500 ppm, more preferably less than 250 ppm, in particular less than 100 ppm, more particularly less than 50 ppm, and the mass content of 1,1,1,3-tetrafluoropropane in said composition is less than 500 ppm, advantageously less than 375 ppm, preferably less than 250 ppm, more preferably less than 100 ppm, in particular less than 50 ppm, more particularly less than 10 ppm.

Preferably, said composition comprises 1,1,1,2,3-pentafluoropropane and 1,1,2-trifluoroethane and/or 1,1,1-trifluoroethane; the mass content of 1,1,1,2,3-pentafluoropropane in said composition is at least 99.5%, advantageously at least 99.8%; and the mass content of 1,1,2-trifluoroethane and/or 1,1,1-trifluoroethane in said composition is less than 50 ppm, advantageously less than 40 ppm, preferably less than 30 ppm, more preferably less than 20 ppm, in particular less than 10 ppm, more particularly less than 1 ppm. Preferably, the content of 1,1,2-trifluoroethane and/or 1,1,1-trifluoroethane is greater than 1 ppb.

Thus, said composition may comprise 1,1,1,2,3-pentafluoropropane, 1,1,1,3-tetrafluoropropane, 1,1,1,2,3,3-hexafluoropropane and 1,1,2-trifluoroethane and/or 1,1,1-trifluoroethane; the mass content of 1,1,1,2,3-pentafluoropropane in said composition is at least 99.5%, advantageously at least 99.8%; the mass content of 1,1,1,2,3,3-hexafluoropropane in said composition is less than 1000 ppm, advantageously less than 750 ppm, preferably less than 500 ppm, more preferably less than 250 ppm, in particular less than 100 ppm, more particularly less than 50 ppm; the mass content of 1,1,1,3-tetrafluoropropane in said composition is less than 500 ppm, advantageously less than 375 ppm, preferably less than 250 ppm, more preferably less than 100 ppm, in particular less than 50 ppm, more particularly less than 10 ppm and the mass content of 1,1,2-trifluoroethane and/or 1,1,1-trifluoroethane in said composition is less than 50 ppm, advantageously less than 40 ppm, preferably less than 30 ppm, more preferably less than 20 ppm, in particular less than 10 ppm, more particularly less than 1 ppm.

Preferably, said composition may be obtained via the process for purifying 1,1,1,2,3-pentafluoropropane according to the present invention.

According to another aspect of the present invention, a composition is provided. Preferably, said composition comprises:

at least 99.5%, advantageously at least 99.8%, by weight of 2,3,3,3-tetrafluoropropene, less than 100 ppm, advantageously less than 75 ppm, preferably less than 50 ppm, more preferably less than 25 ppm, in particular less than 10 ppm, more particularly less than 5 ppm of 3,3,3-trifluoropropene, less than 100 ppm, advantageously less than 75 ppm, preferably less than 50 ppm, more preferably less than 25 ppm, in particular less than 10 ppm of 1,2,3,3,3-pentafluoropropene, less than 200 ppm, advantageously less than 150 ppm, preferably less than 100 ppm, more preferably less than 75 ppm, in particular less than 50 ppm of 1,1,2-trifluoroethane and/or 1,1,1-trifluoroethane, and less than 20 ppm, advantageously less than 15 ppm, preferably less than 10 ppm, in particular less than 5 ppm of 1,1,1,2,3-pentafluoropropane, on the basis of the total weight of the composition.

Preferably, said composition comprises 2,3,3,3-tetrafluoropropene and 3,3,3-trifluoropropene; the mass content of 2,3,3,3-tetrafluoropropene in said composition is at least 99.5%, advantageously at least 99.8%; and the mass content of 3,3,3-trifluoropropene in said composition is less than 100 ppm, advantageously less than 75 ppm, preferably less than 50 ppm, more preferably less than 25 ppm, in particular less than 10 ppm, more particularly less than 5 ppm.

Preferably, said composition comprises 2,3,3,3-tetrafluoropropene and 1,2,3,3,3-pentafluoropropene; the mass content of 2,3,3,3-tetrafluoropropene in said composition is at least 99.5%, advantageously at least 99.8%; and the mass content of 1,2,3,3,3-pentafluoropropene in said composition is less than 100 ppm, advantageously less than 75 ppm, preferably less than 50 ppm, more preferably less than 25 ppm, in particular less than 10 ppm.

Preferably, said composition comprises 2,3,3,3-tetrafluoropropene, 3,3,3-trifluoropropene and 1,2,3,3,3-pentafluoropropene; the mass content of 2,3,3,3-tetrafluoropropene in said composition is at least 99.5%, advantageously at least 99.8%; the mass content of 3,3,3-trifluoropropene in said composition is less than 100 ppm, advantageously less than 75 ppm, preferably less than 50 ppm, more preferably less than 25 ppm, in particular less than 10 ppm, more particularly less than 5 ppm; and the mass content of 1,2,3,3,3-pentafluoropropene in said composition is less than 100 ppm, advantageously less than 75 ppm, preferably less than 50 ppm, more preferably less than 25 ppm, in particular less than 10 ppm.

Preferably, said composition comprises 2,3,3,3-tetrafluoropropene and 1,1,2-trifluoroethane and/or 1,1,1-trifluoroethane; the mass content of 2,3,3,3-tetrafluoropropene in said composition is at least 99.5%, advantageously at least 99.8%; and the mass content of 1,1,2-trifluoroethane and/or 1,1,1-trifluoroethane in said composition is less than 200 ppm, advantageously less than 150 ppm, preferably less than 100 ppm, more preferably less than 75 ppm, in particular less than 50 ppm.

Preferably, said composition comprises 2,3,3,3-tetrafluoropropene, 3,3,3-trifluoropropene, 1,2,3,3,3-pentafluoropropene and 1,1,2-trifluoroethane and/or 1,1,1-trifluoroethane; the mass content of 2,3,3,3-tetrafluoropropene in said composition is at least 99.5%, advantageously at least 99.8%; the mass content of 3,3,3-trifluoropropene in said composition is less than 100 ppm, advantageously less than 75 ppm, preferably less than 50 ppm, more preferably less than 25 ppm, in particular less than 10 ppm, more particularly less than 5 ppm; the mass content of 1,2,3,3,3-pentafluoropropene in said composition is less than 100 ppm, advantageously less than 75 ppm, preferably less than 50 ppm, more preferably less than 25 ppm, in particular less than 10 ppm; and the mass content of 1,1,2-trifluoroethane and/or 1,1,1-trifluoroethane in said composition is less than 200 ppm, advantageously less than 150 ppm, preferably less than 100 ppm, more preferably less than 75 ppm, in particular less than 50 ppm.

In particular, in any one of the above compositions comprising 2,3,3,3-tetrafluoropropene, they may be free of 1,1,1,2,3-pentafluoropropane.

Alternatively, in any one of the above compositions comprising 2,3,3,3-tetrafluoropropene, they may comprise less than 20 ppm, advantageously less than 15 ppm, preferably less than 10 ppm, in particular less than 5 ppm of 1,1,1,2,3-pentafluoropropane.

Preferably, said composition may be obtained via the process for producing 2,3,3,3-tetrafluoropropene according to the present invention.

FIG. 1a schematically represents a particular embodiment of the present invention. In particular, FIG. 1 represents a process for purifying 1,1,1,2,3-pentafluoropropane and for producing 2,3,3,3-tetrafluoropropene according to a particular embodiment of the present invention. The composition A1 as described above is conveyed to the distillation column 2 to form a stream B1' recovered at the bottom of the distillation column 2 and a stream B1 recovered at the top of the distillation column 2. The stream B1 is conveyed via the pipe 3 to an incineration device 4. The stream B1' is conveyed via the pipe 5 to the distillation column 6. The stream B1' is distilled to form and to recover, at the top of the distillation column, a stream B2 as described in the present application, and to form and to recover, at the bottom of the distillation column, a stream B2' as described in the present application. The stream B2' is conveyed via the pipe 10 to an incineration device 9. Stream B2 is conveyed via the pipe 7 to a dehydrofluorination reactor 8 enabling the dehydrofluorination of the 1,1,1,2,3-pentafluoropropane to give 2,3,3,3-tetrafluoropropene. A stream C1 according to the present invention is thus obtained at 8. The stream C1 is finally conveyed via the pipe 11 to a purification device 12 preferably comprising at least one distillation column, in particular at least two distillation columns. The purification device 12 enables the formation of the stream C3 as described in the present application.

Figure 1B:
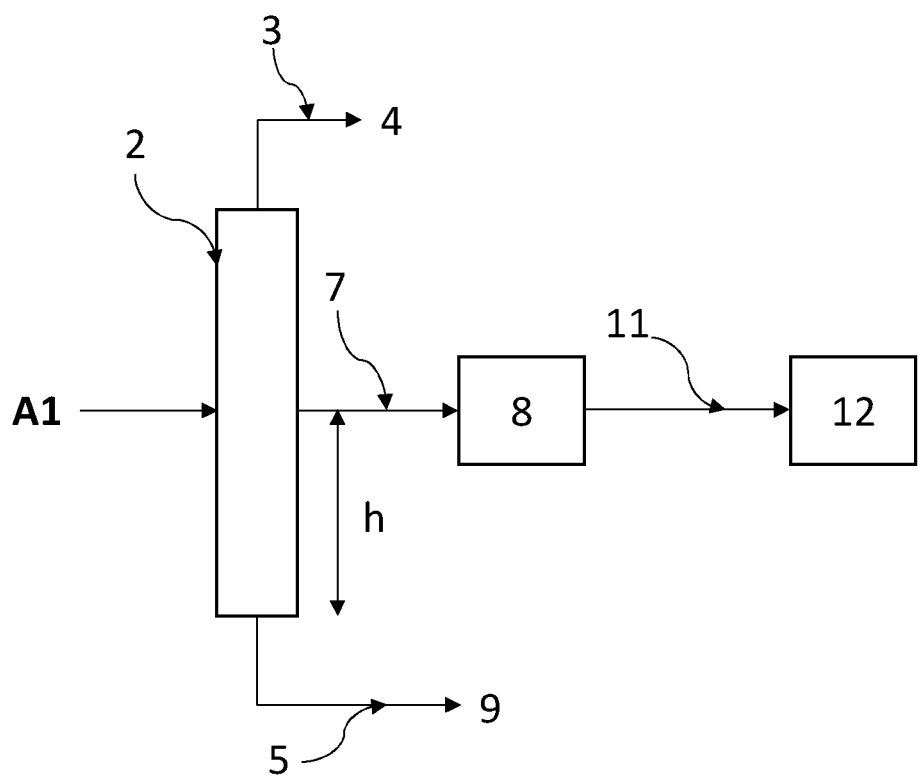

FIG. 1b schematically represents a particular embodiment of the present invention. In particular, FIG. 1b represents a process for purifying 1,1,1,2,3-pentafluoropropane and for producing 2,3,3,3-tetrafluoropropene according to another particular embodiment of the present invention. The composition A1 as described above is conveyed to the distillation column 2. The distillation column 2 is, in this case, a dividing-wall distillation column. Thus, said third stream comprising 1,1,1,2,3,3-hexafluoropropane, 1,1,2-trifluoroethane, 1,1,1-trifluoroethane and 1,1,1,2-tetrafluoropropane is recovered at the top of the distillation column. This stream is conveyed via the pipe 3 to an incineration device 4. Said second stream comprising 1,1,1,3-tetrafluoropropane is recovered at the bottom of the distillation column. This stream is conveyed via the pipe 5 to an incineration device 9. Finally, said first stream comprising 1,1,1,2,3-pentafluoropropane is recovered at a height h of the distillation column 2 located between the top and the bottom of the distillation column. Said first stream is conveyed via the pipe 7 to a dehydrofluorination reactor 8 enabling the dehydrofluorination of the 1,1,1,2,3-pentafluoropropane to give 2,3,3,3-tetrafluoropropene. A stream C1 according to the present invention is thus obtained at 8. The stream C1 is finally conveyed via the pipe 11 to a purification device 12 preferably comprising at least one distillation column, in particular at least two distillation columns. The purification device 12 enables the formation of the stream C3 as described in the present application.

Figure 2A:
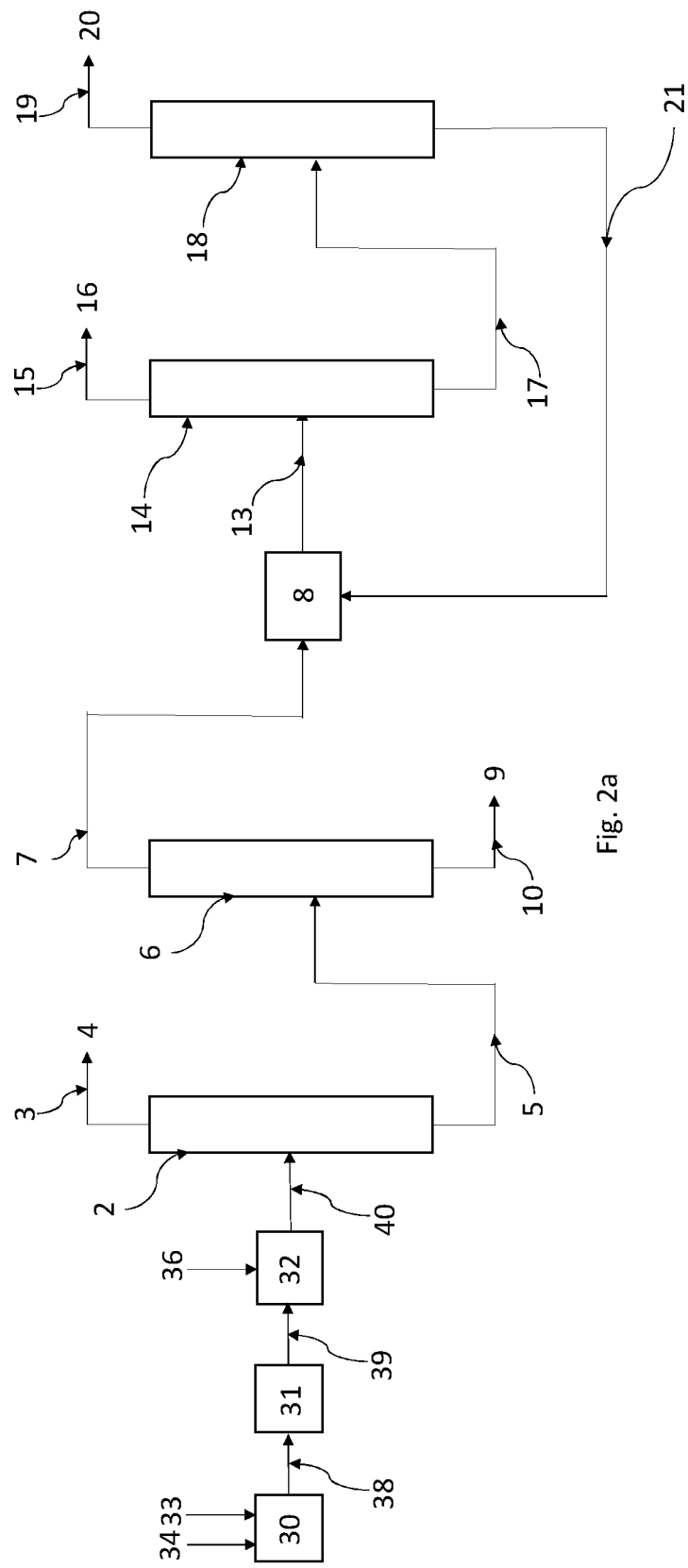
FIGS. 2a and 2b schematically represent a process for producing 2,3,3,3-tetrafluoropropene from hexafluoropropene according to a particular embodiment of the present invention.
Figure 2B:
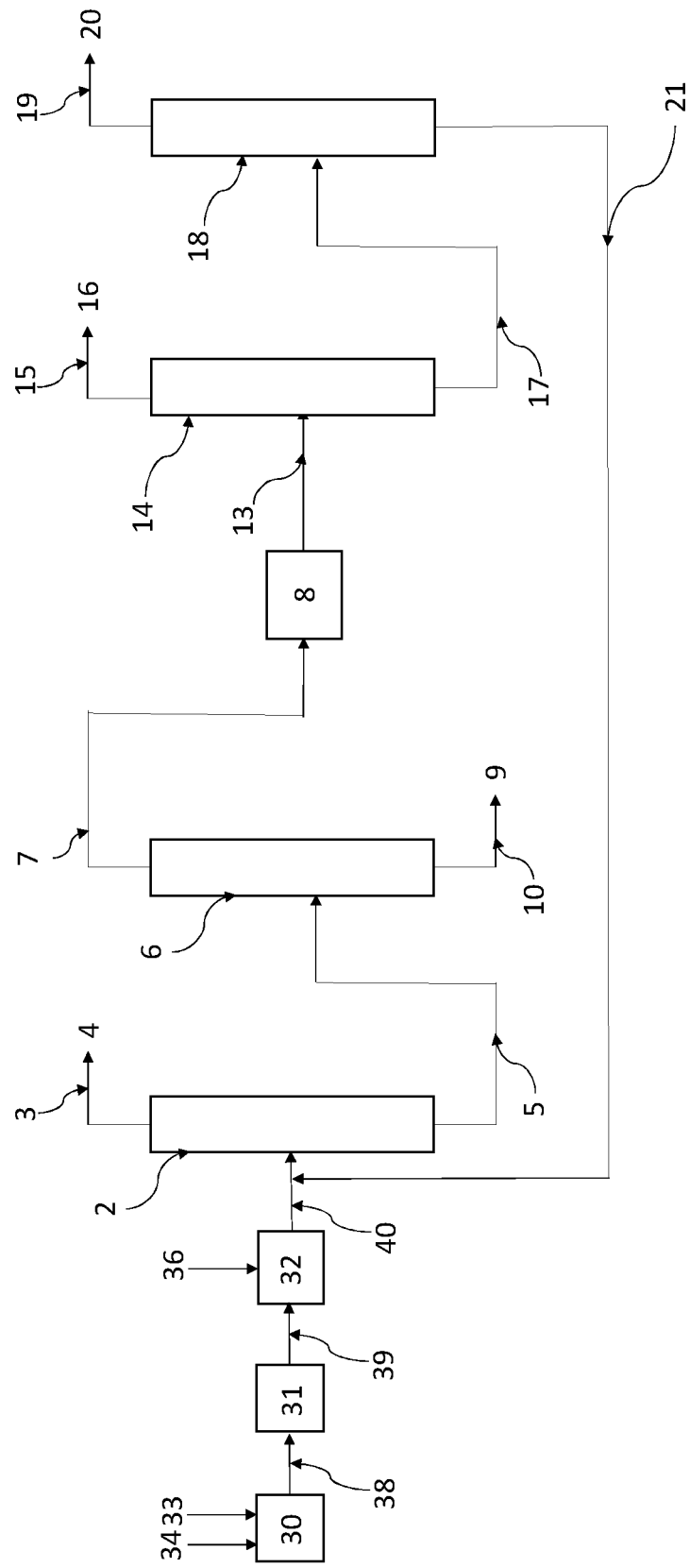
Figure 3A:
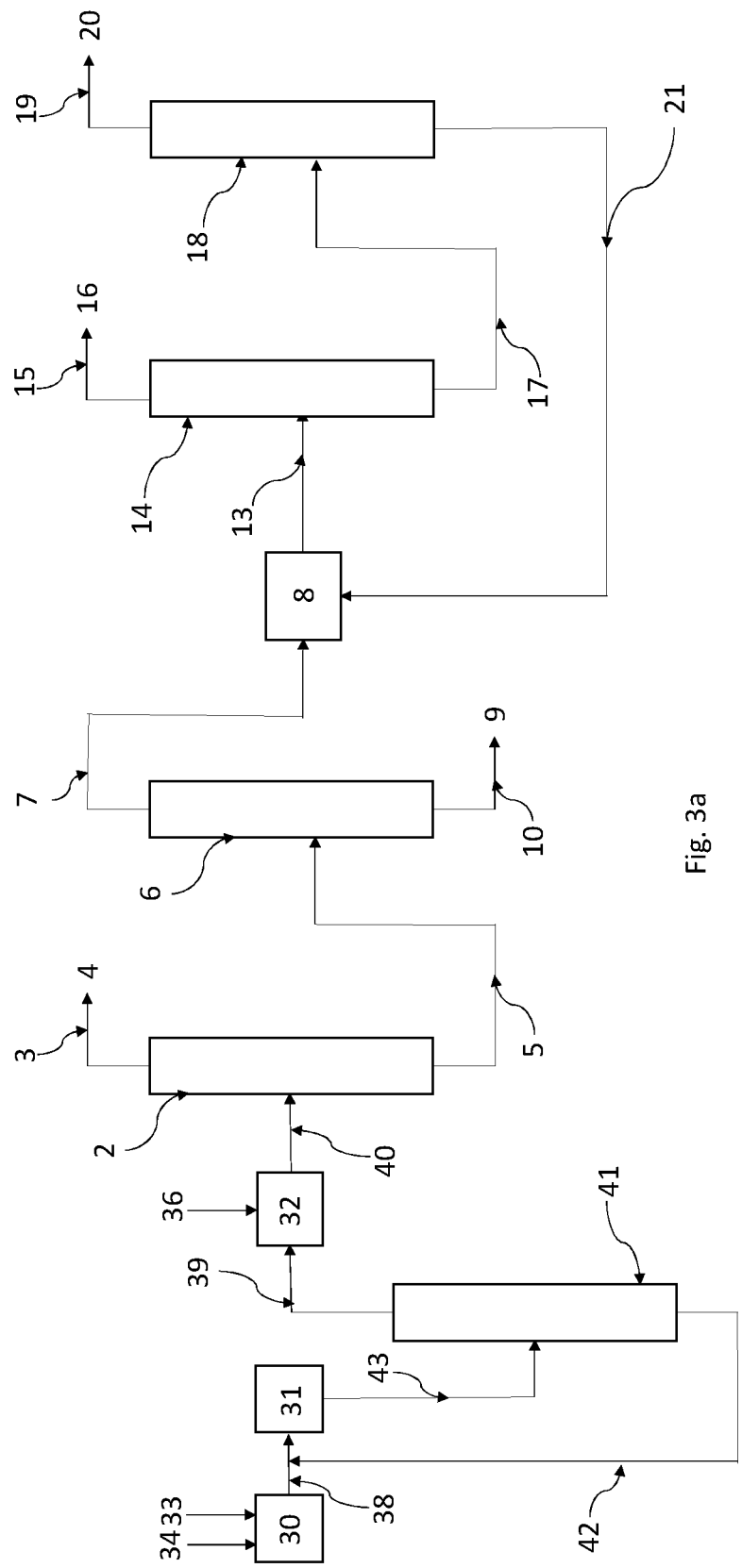
FIGS. 3a, 3b, 4a and 4b schematically represent a process for producing 2,3,3,3-tetrafluoropropene from hexafluoropropene according to a particular embodiment of the present invention including the purification of 1,2,3,3,3-tetrafluoropropene and of 1,1,1,2,3-pentafluoropropane.
Figure 3B:
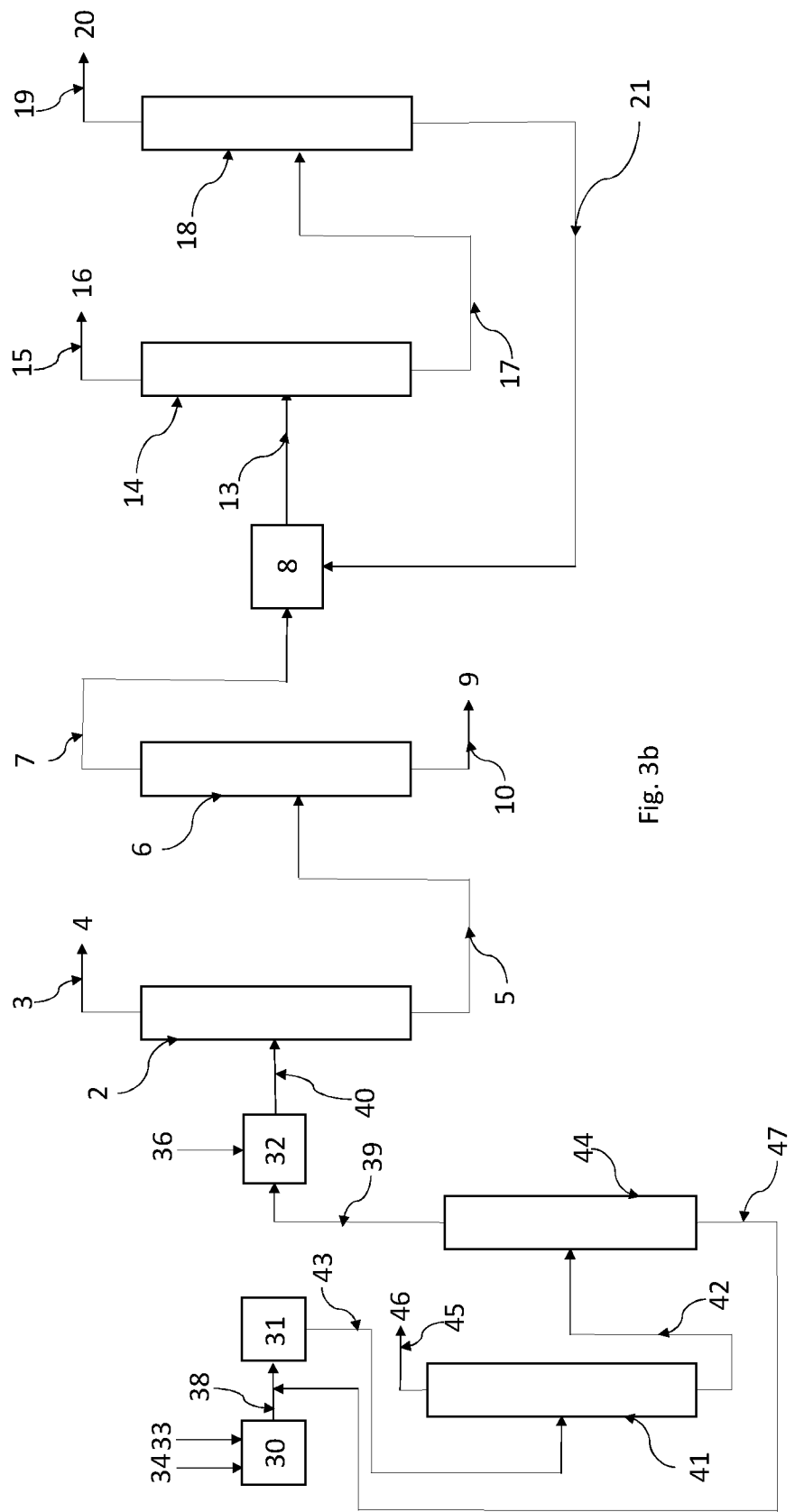
Figure 4A:
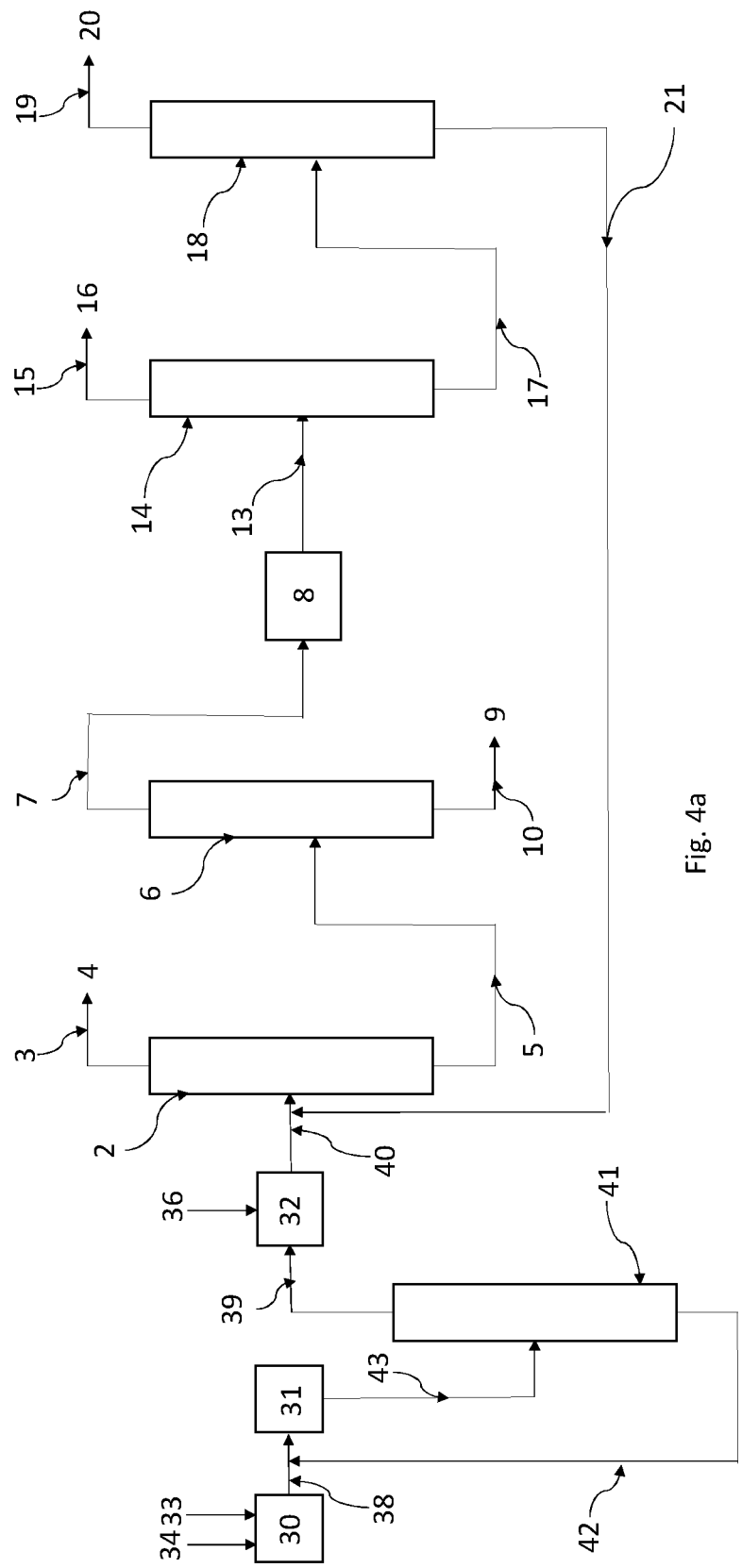
Figure 4B:
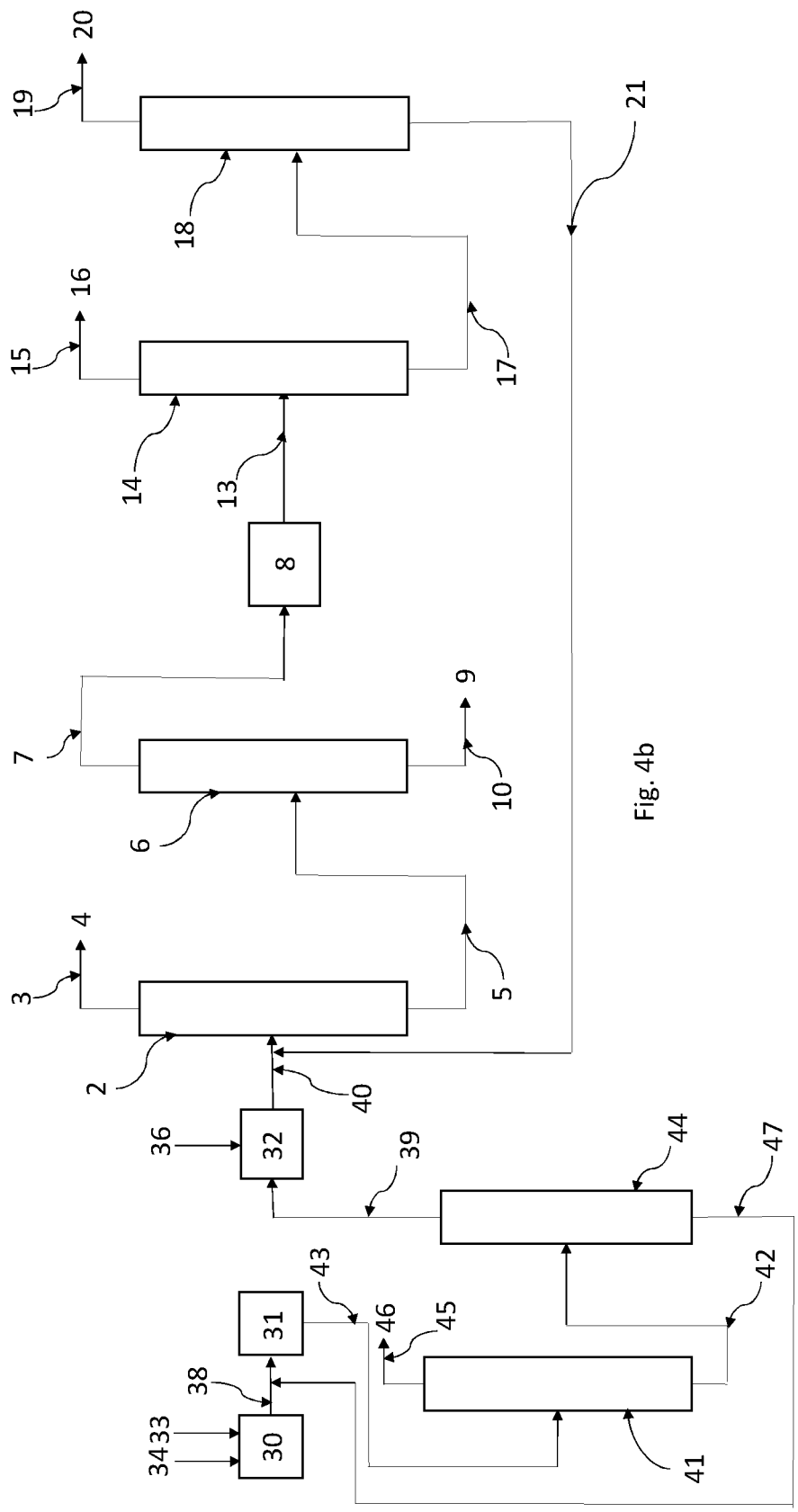

FIGS. 2a and 2b schematically represent a particular embodiment of the present invention. In particular, FIGS. 2a and 2b represent a process for producing 2,3,3,3-tetrafluoropropene including the process for purifying 1,1,1,2,3-pentafluoropropane according to the present invention. In a reactor 30, hexafluoropropene (noted 34) and hydrogen (noted 33) are placed in contact to form a stream comprising 1,1,1,2,3,3-hexafluoropropane. This stream is conveyed via the pipe 38 to the reactor 31. The 1,1,1,2,3,3-hexafluoropropane is dehydrofluorinated in the reactor 31 to form a stream comprising 1,2,3,3,3-pentafluoropropene. This stream is conveyed to the reactor 32 to be placed in contact with hydrogen (noted 36) to form the composition A1 according to the present invention. The composition A1 is conveyed via the pipe 40 to the distillation column 2 to form a stream B1' recovered at the bottom of the distillation column 2 and a stream B1 recovered at the top of the distillation column 2. The stream B1 is conveyed via the pipe 3 to an incineration device 4. The stream B1' is conveyed via the pipe 5 to the distillation column 6. The stream B1' is distilled to form and to recover, at the top of the distillation column, a stream B2 as described in the present application, and to form and to recover, at the bottom of the distillation column, a stream B2' as described in the present application. The stream B2' is conveyed via the pipe 10 to an incineration device 9. The stream B2 is conveyed via the pipe 7 to a dehydrofluorination reactor 8 enabling the dehydrofluorination of the 1,1,1,2,3-pentafluoropropane to 2,3,3,3-tetrafluoropropene. A stream C1 according to the present invention is thus obtained at 8. The stream C1 is finally conveyed via the pipe 13 to the distillation column 14 to form said stream C2 at the top of the distillation column and to form said stream C2' at the bottom of the distillation column. The stream C2 is conveyed via the pipe 15 to an incineration device 16. The stream C2' is conveyed via the pipe 17 to the distillation column 18 to recover said stream C3 at the top of the distillation column and said stream C3' at the bottom of the distillation column. Said stream C3 comprising 2,3,3,3-tetrafluoropropene is conveyed via the pipe 19 to a storage device 20. Said stream C3' comprising 1,1,1,2,3-pentafluoropropane is recycled into the reactor 8 (FIGS. 2a, 3a, 3b) or recycled to the outlet of the reactor 32 (FIGS. 2b, 4a and 4b).

The stream obtained from the reactor 31 and comprising 1,2,3,3,3-pentafluoropropene may be purified before being conveyed to the reactor 32. This is represented in FIGS. 3a, 3b, 4a and 4b. In FIGS. 3a and 4a, the stream comprising 1,2,3,3,3-pentafluoropropene, at the outlet of the reactor 31, is conveyed via the pipe 43 to the distillation column 41. The purified 1,2,3,3,3-pentafluoropropene is recovered at the top of the distillation column and conveyed via the pipe 39 to the reactor 32. This stream may also comprise 1,1,1,2-tetrafluoroethane, 1,1,2-trifluoroethane and 1,1,1-trifluoroethane forming the stream D1 mentioned above. The unreacted 1,1,1,2,3,3-hexafluoropropane (stream D2) in the reactor 31 is recovered at the bottom of the distillation column 41 to be conveyed via the pipe 42 to the inlet of the reactor 31. FIGS. 3b and 4b represent an embodiment in which the stream obtained from the reactor 31 is purified by means of two distillation columns. The stream comprising 1,2,3,3,3-pentafluoropropene, at the outlet of the reactor 31, is conveyed via the pipe 43 to the distillation column 41. The stream D3 comprising 1,1,2-trifluoroethylene is recovered at the top of the distillation column. The stream D3 may be upgraded or incinerated at 46 via the pipe 45. At the bottom of the distillation column 41, a stream D3' comprising 1,2,3,3,3-pentafluoropropene and 1,1,1,2,3,3-hexafluoropropane is recovered, to be conveyed to the distillation column 44 via the pipe 42. The stream D4 comprising 1,2,3,3,3-pentafluoropropene is recovered at the top of the distillation column and conveyed via the pipe 39 to the reactor 32. The stream D4' comprising 1,1,1,2,3,3-hexafluoropropane is recovered at the bottom of the distillation column and recycled via the pipe 47 to the inlet of the reactor 31.

Example

The 1,2,3,3,3-pentafluoropropene obtained by dehydrofluorination of the 1,1,1,2,3,3-hexafluoropropane which is itself obtained by hydrogenation of hexafluoropropene is placed in contact with hydrogen in the gas phase in a super-stoichiometric amount in an adiabatic reactor in the presence of a catalyst comprising palladium supported on alpha-alumina (0.2% by weight of Pd) to form 1,1,1,2,3-pentafluoropropane. The temperature at the reactor inlet is 80° C. and the pressure is 2.8 bara. The hydrogen/1225ye mole ratio at the reactor inlet is between 2 and 20. The composition of the stream obtained at the hydrogenation reactor outlet is given in table 1 below.

TABLE 1

| % HF | ppm H$_2$O | % 245eb | % 254eb | % 1225ye-Z | % 143 + 143a | % 236ea | % 254fb | % Other |
|---|---|---|---|---|---|---|---|---|
| 0.20 | 613 | 93.44 | 3.84 | 0.18 | 1.76 | 0.02 | 0.052 | 0.45 |

Other: notably 1234zeE, 263fb, 245fa, 245ea, 1233zd-E

The stream comprising 1,1,1,2,3-pentafluoropropane, corresponding to the composition A1 according to a particular embodiment of the present invention, is subjected to a distillation comprising two distillation columns in series. The first distillation column is maintained at a pressure of from 5 to 10 bara for a distillation column head temperature of from 45 to 75° C. The stream obtained at the bottom of the distillation column corresponds to the stream B1' according to a particular embodiment of the present invention. The composition of the stream thus obtained is given in table 2 below.

TABLE 2

| % HF | ppm H$_2$O | % 245eb | ppm 254eb | ppm 1225ye-Z | ppm 143 + 143 a | ppm 236ea | ppm 254fb | ppm Other |
|---|---|---|---|---|---|---|---|---|
| 0.04 | 323 | 99.81 | 0 | 0 | 5 | 20 | 547 | <560 |

Other: notably 1234zeE, 263fb, 245fa, 245ea, 1233zd-E

The second distillation column is maintained at a pressure of from 3 to 6 bara for a distillation column head temperature of from 50 to 80° C. The stream recovered at the top of the second distillation column comprises purified 1,1,1,2,3-pentafluoropropane, corresponding to the stream B2 according to a particular embodiment of the present invention. The composition of the stream thus obtained is given in table 3 below.

TABLE 3

| % HF | ppm H$_2$O | % 245eb | ppm 254eb | ppm 1225ye-Z | ppm 143 + 143a | ppm 236ea | ppm 254fb | ppm Other |
|---|---|---|---|---|---|---|---|---|
| 0.01 | 320 | 99.92 | 0 | 0 | 5 | 95 | 3 | <300 |

Other: notably 1234zeE, 263fb, 245fa, 245ea, 1233zd-E

The 1,1,1,2,3-pentafluoropropane thus purified is subjected to a dehydrofluorination step to give 2,3,3,3-tetrafluoropropene. The gas stream obtained from the dehydrofluorination step comprising 2,3,3,3-tetrafluoropropene is subjected to a purification step comprising two distillation columns to obtain 2,3,3,3-tetrafluoropropene in a purity of greater than 99.8% by weight, preferably greater than 99.9% by weight. The composition of the stream thus obtained is given in table 4 below.

TABLE 4

| % 1234yf | % 245eb | % 1243zf | % 1132 | % 1225ye(E + Z) | % 1234ze-E | % 143 + 143a |
|---|---|---|---|---|---|---|
| 99.9078 | Not detected | 0.0004 | 0.0010 | 0.0014 | 0.0122 | 0.0006 |

The process according to the present invention thus enables the production of high-purity 1,1,1,2,3-pentafluoropropane, but also high-purity 2,3,3,3-tetrafluoropropene.

The invention claimed is:

1. A composition comprising:
   at least 99.5% by weight of 1,1,1,2,3-pentafluoropropane,
   from 1 ppb to 500 ppm of 1,1,1,3-tetrafluoropropane;
   less than 1000 ppm of 1,1,1,2,3,3-hexafluoropropane;
   from 1 ppb to 50 ppm of 1,1,2-trifluoroethane and/or 1,1,1-trifluoroethane;
   less than 100 ppm of 1,1,1,2-tetrafluoropropane;
   on the basis of the total weight of the composition.

2. A composition comprising 2,3,3,3-tetrafluoropropene; 3,3,3-trifluoropropene; 1,2,3,3,3-pentafluoropropene; and 1,1,2-trifluoroethane and/or 1,1,1-trifluoroethane, wherein the composition comprises:
 at least 99.5% by weight of 2,3,3,3-tetrafluoropropene,
 less than 100 ppm of 3,3,3-trifluoropropene,
 less than 100 ppm of 1,2,3,3,3-pentafluoropropene,
 less than 200 ppm of 1,1,2-trifluoroethane and/or 1,1,1-trifluoroethane, and
 less than 20 ppm of 1,1,1,2,3-pentafluoropropane,
 on the basis of the total weight of the composition.

3. The composition of claim 1 comprising from 0 ppm to 100 ppm of 1,1,1,2,3,3-hexafluoropropane on the basis of the total weight of the composition.

4. The composition of claim 3 comprising from 0 ppm to 25 ppm of 1,1,1,2,3,3-hexafluoropropane on the basis of the total weight of the composition.

5. The composition of claim 1 comprising from 0 ppm to 10 ppm 1,1,1,3-tetrafluoropropane on the basis of the total weight of the composition.

* * * * *